(12) United States Patent

Winoto et al.

(10) Patent No.: US 7,892,539 B2
(45) Date of Patent: Feb. 22, 2011

(54) MODULATION OF AN INNATE IMMUNE RESPONSE BY ALTERING TRIAL-R SIGNALING

(75) Inventors: Astar Winoto, Berkeley, CA (US); Gretchen Elizabeth Diehl, Berkeley, CA (US); Herman Heng Yue, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 443 days.

(21) Appl. No.: 11/088,459

(22) Filed: Mar. 23, 2005

(65) Prior Publication Data

US 2005/0216960 A1    Sep. 29, 2005

Related U.S. Application Data

(60) Provisional application No. 60/556,188, filed on Mar. 24, 2004.

(51) Int. Cl.
*A61K 39/00* (2006.01)
*A61K 39/395* (2006.01)
*G01N 33/53* (2006.01)
*C07K 16/00* (2006.01)
*C07K 16/22* (2006.01)
*C07K 16/24* (2006.01)
*C07K 16/28* (2006.01)

(52) U.S. Cl. .................. 424/130.1; 435/7.1; 530/387.1; 530/388.22; 530/388.23; 530/388.24; 530/389.1; 530/389.2; 514/2

(58) Field of Classification Search .................. None
See application file for complete search history.

(56) References Cited

U.S. PATENT DOCUMENTS

| | | | |
|---|---|---|---|
| 6,046,048 A * | 4/2000 | Ashkenazi et al. | 435/331 |
| 6,342,363 B1 * | 1/2002 | Ni et al. | 435/7.2 |
| 6,433,147 B1 * | 8/2002 | Ni et al. | 530/387.3 |
| 6,743,625 B2 * | 6/2004 | Ni et al. | 435/325 |
| 6,872,568 B1 * | 3/2005 | Ni et al. | 435/326 |
| 2002/0072091 A1 | 6/2002 | Ni et al. | |
| 2005/0129616 A1 * | 6/2005 | Salcedo et al. | 424/1.49 |

OTHER PUBLICATIONS

Halaas et al. Lipopolysaccharide induces expression of APO2 Ligand/TRIAL in human monocytes and macrophages. Scand J Immunol 51: 244-250, 2000.*
Almasan et al. Apo2L/TRAIL: apoptosis signaling, biology, and potential for cancer therapy. Cytokine Growth Factor Rev 14: 237-348, 2003.*
Chaudhary et al. Death Receptor 5, a new member of the TNFR family, and DR4 induce FADD-dependent apoptosis and activate the NF-KB pathway. Immunity 7: 821-830, 1997.*
Phillips et al. TRAIL (Apo2L) and TRAIL receptors in human placentas: implications for immune privilege. J Immunol 162: 6053-6059, 1999.*
Kuang et al. FADD is required for DR4- and DR5- mediated apoptosis. J Biol Chem 275(33): 25065-25068, 2000.*
Elgert, K. Immunology, understanding the immune system. New York: Wiley-Liss, Inc., 1996; pp. 5-7.*
Elgert, K. Immunology, understanding the immune system. New York: Wiley-Liss, Inc., 1996; pp. 218-224.*
"Septicemia" definition from MedlinePlus Medical Encyclopedia; downloaded on Nov. 4, 2009 from www.nlm.nih.gov/medlineplus/ency/article/001355.htm.*
Thompson, C.B. Apoptosis in the pathogenesis and treatment of disease. Science 267: 1456-1462, 1995.*
Mundt et al. Involvement of TRAIL and its receptors in viral hepatitis. FASEB J 17(1): 94-96, 2003.*
Clarke et al. Reovirus-induced apoptosis: A minireivew. Apoptosis 8(2): 141-150, 2003.*
Janssen et al. Hepatitis B virus enhances tumor necrosis factor-related apoptosis-inducing ligand (TRAIL) cytotoxicity by increasing TRAIL-R1/death receptor 4 expression. J Hepatol 39: 414-420, 2003.*
Baker et al., Modulation of Life and Death by the TNF Receptor Superfamily, (1998), *Oncogene*, 17(25):3261-70.
Gravestein et al., Tumor Necrosis Factor Receptor Family Members in the Immune System, (1998), *Semin Immunol*, 10(6):423-34.
Walczak et al., Tumoricidal Activity of Tumor Necrosis Factor-Related Apoptosis-Inducing Ligand in vivo, (1999), *Nature Medicine*, 5:157-163.
Diehl et al., TRAIL-R as a Negative Regulator of Innate Immune Cell Responses, 2004, Immunity, 21(21): 877-889.
Kaplan et al., TRAIL (APO2 Ligand) and TWEAK (APO3 Ligand) Mediate CD4+ T Cell Killing of an Tigen-Presenting Macrophages[1], The Journal of Immunology, 1999, 164: 2897-2904.

* cited by examiner

*Primary Examiner*—Bridget E Bunner
(74) *Attorney, Agent, or Firm*—Bozicevic, Field & Francis LLP; Pamela J. Sherwood

(57) ABSTRACT

Methods and composition are provided for modulating innate immunity by modulating activation of the TRAIL receptor. Signaling through the TRAIL-R inhibits the responsiveness of cells including dendritic cells, macrophages, and the like. The activity of these cells is increased or decreased by the administration of agents that inhibit or activate TRAIL-R signaling. Innate immunity includes the production of cytokines that act on the immune system.

8 Claims, 12 Drawing Sheets

FIG. 1D

3rd exon / 7th exon

ACAGTCTGTAAGGAAG/GAACCTGGCAAGACTCAGAAAACAGGAAAGAAGTTGCTGGTTCCGGTAAACGGAAACGACTCAGCTGA
(SEQ ID NO:4)

T V C K E   E P G K T Q K T G K K L L V P V N G  N D S A D
(SEQ ID NO:5)

T V C K E G   T W Q D S E N R K E V A G S G K R K R L S *
(SEQ ID NO:6)

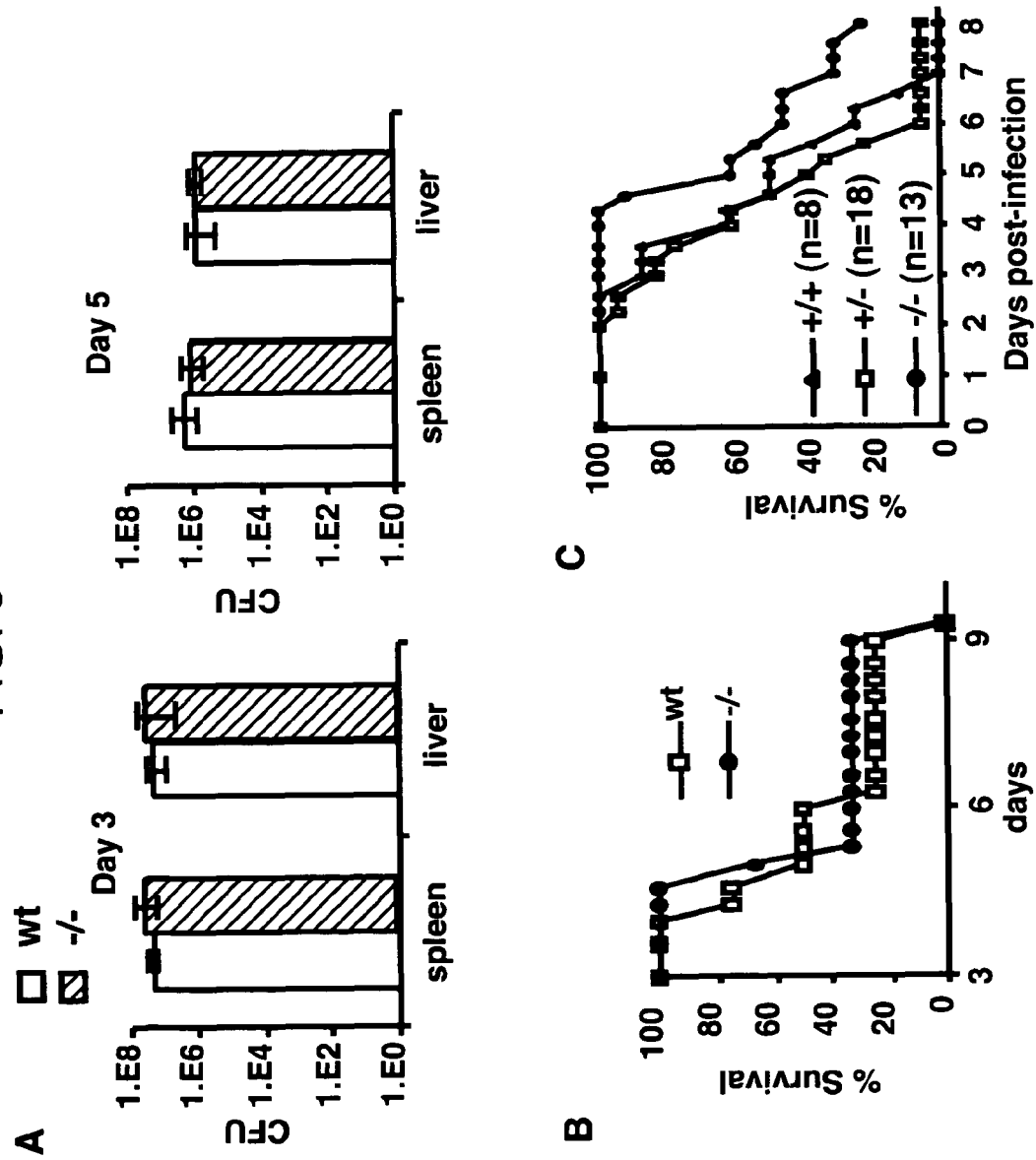

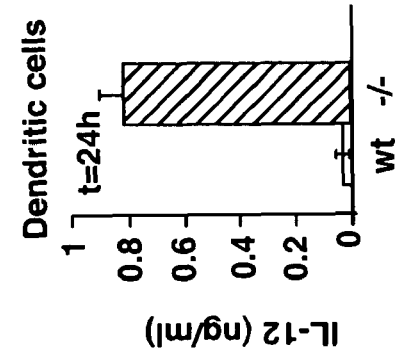
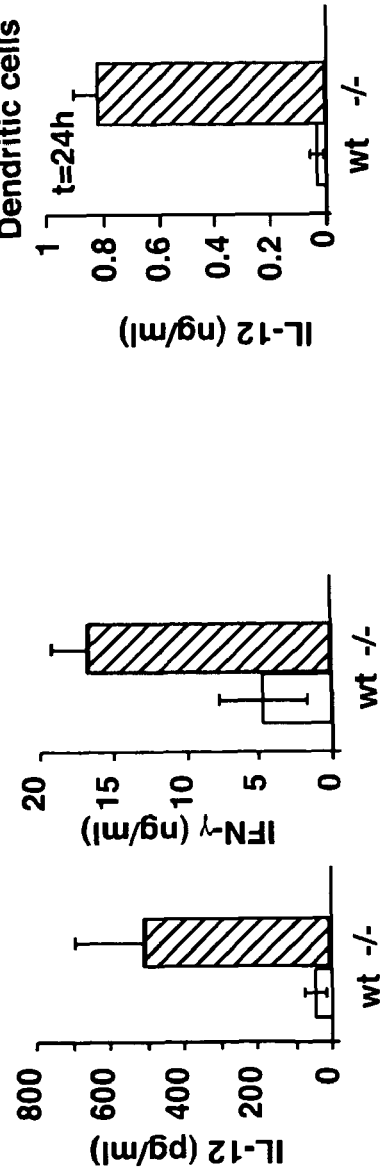
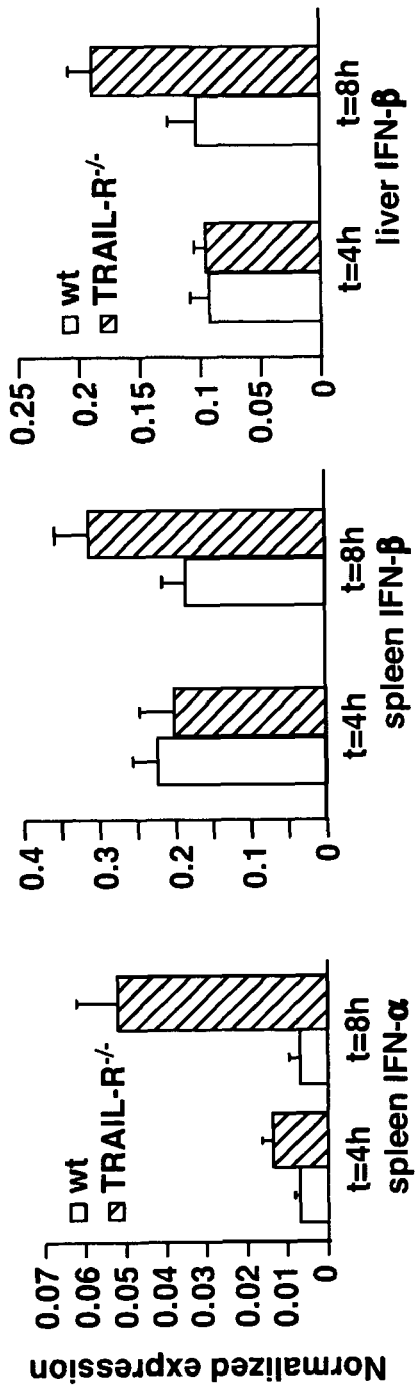
FIG. 4C
FIG. 4D
FIG. 4E

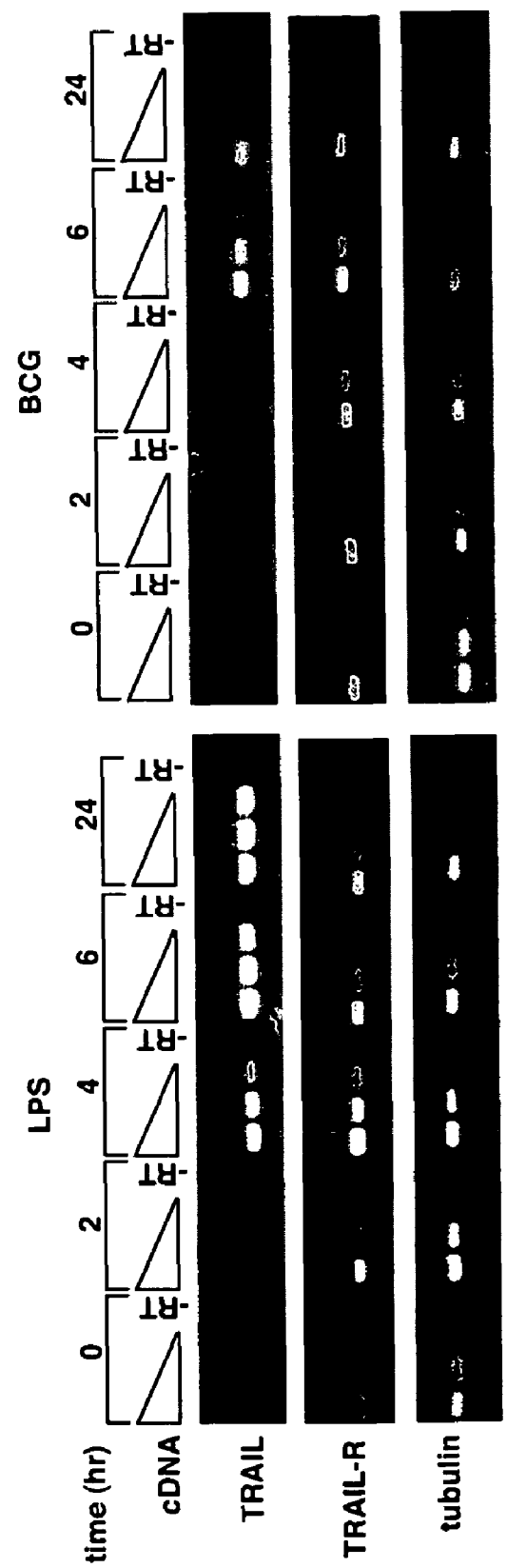

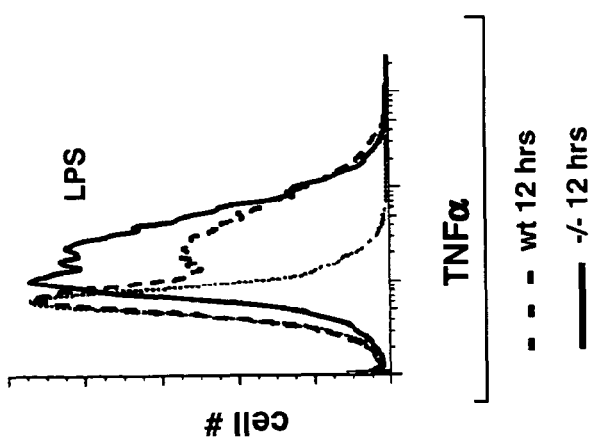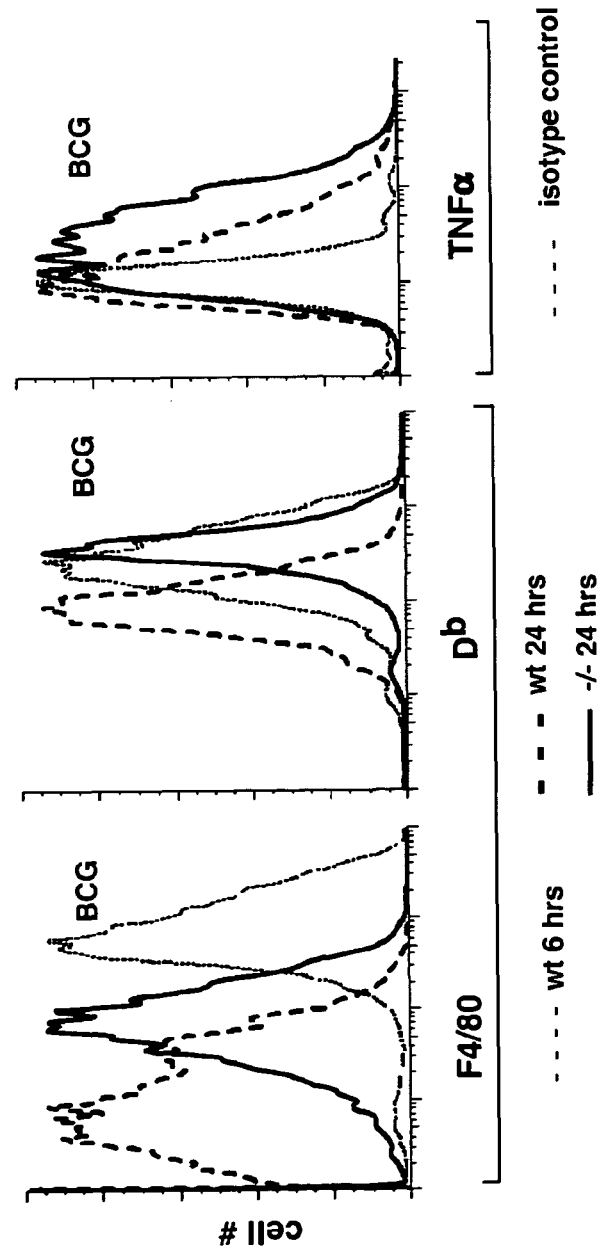

MODULATION OF AN INNATE IMMUNE RESPONSE BY ALTERING TRIAL-R SIGNALING

This invention was made with Government support under contract CA92000 awarded by the National Institutes of Health. The Government has certain rights in this invention.

BACKGROUND

Tumor necrosis factor (TNF) is the prototypic member of a family of cytokines, which interact with their receptors to carry out diverse functions. Some TNF-receptor family members, termed the "death receptors", possess an intracellular "death domain", and have the unique ability to transmit an intracellular death signal. TRAIL (Tumor necrosis factor related apoptosis inducing ligand), also known as Apo2L, was originally identified through its homology to TNF, FasL, and other members of the TNF superfamily. Addition of TRAIL induces apoptosis of many tumor cell lines but interestingly, has no apoptotic effect on most normal non-transformed cells. In humans, four members of the TNF receptor superfamily can bind TRAIL: TRAIL-R1 (DR4), TRAIL-R2 (DR5), TRAIL-R3 (DcR1, TRID), and TRAIL-R4 (DcR2, TRUNDD).

TRAIL-R1 (DR4) and -R2 (DR5) possess an intracellular tail containing a conserved motif known as the death domain. As in TNF-RI and Fas, this domain allows interaction with the downstream adapter protein(s) to initiate apoptotic signals. In contrast, TRAIL-R3 possesses a truncated cytoplasmic tail lacking a death domain and TRAIL-R4 exists as a GPI-linked protein. These latter two receptors are thought to function as decoy proteins that can inhibit signaling through TRAIL-R1 and -R2. The fifth receptor for TRAIL, osteoprotegerin, is a soluble protein that participates in regulation of bone density. Osteoprotegerin can inhibit TRAIL-mediated apoptosis in vitro but its functional relationship with TRAIL in vivo is not clear. In mice, there is only one full-length receptor, TRAIL-R (mDR4/5, mTRAILR2, mKILLER), which is equally homologous to human DR4 and DR5. Like its human homologues, this receptor is capable of signaling apoptosis following either over-expression or receptor ligation by TRAIL. Two murine decoy receptors (mDcTRAILR1 and mDcTRAILR2) have also been recently reported. They lack a death domain and do not induce apoptosis in sensitive cells.

The ability to preferentially signal apoptosis in transformed cells has led to numerous studies of the mechanism of TRAIL-R signaling. TRAIL-R can induce apoptosis in a FADD dependent manner. Similar to Fas, only FADD and caspase-8 were found in the TRAIL-R signaling complex in some studies. In contrast, others have reported the recruitment of TRADD and RIP to the signaling complex and showed that TRAIL-R, like TNF-R, can activate NF-κB and JNK. These discrepancies could be due to differences in cell lines or cell type-specific signaling. However, the similarity to TNF receptor signaling has led to speculation that sensitivity to TRAIL induced apoptosis may be regulated by expression of anti-apoptotic factors downstream of NF-κB or by more proximal factors such as c-FLIP, which inhibits caspase-8 activation. In addition, mitochondrial factors such as SMAC/Diablo have been implicated in regulating TRAIL-R induced apoptosis. Indeed, it may be a combination of different cytoplasmic factors, which regulate sensitivity to TRAIL-R induced apoptosis.

While the ability to induce apoptosis in transformed cells is well established, the role of TRAIL and its receptor(s) in normal mammalian physiology is not understood. TRAIL has been shown to be expressed on the surface of Natural Killer (NK) and T cells, macrophages and dendritic cells in an activation dependent manner; however, its function remains unclear. Cells normally resistant to TRAIL induced apoptosis can become sensitive following viral infection, and treatment of mice with neutralizing anti-TRAIL antibodies enhances their sensitivity to encephalomyocarditis virus (EMCV). TRAIL-deficient animals display increased susceptibility to tumor metastasis and autoimmune disease progression as well as defects in negative selection, although this latter finding is controversial. These data suggest that TRAIL may play roles in tumor surveillance, regulation of autoimmunity, and T cell development.

Relevant Literature

A review of the TNF receptor superfamily may be found in Baker and Reddy (1998) *Oncogene* 17(25):3261-70. The tumor necrosis factor receptor (TNF-R) superfamily represents a growing family, with over 20 members having been identified thus far in mammalian cells. These proteins share significant homology in their extracellular ligand binding domains and intracellular effector (death) domains. Death signals seem to be associated with the activation of the caspase pathway. In addition to cell death, some members of this family, especially TNF-R, can signal activation of transcription factors (such as Jun and NF-κB) and inflammatory responses. Gravestein and Borst (1998) *Semin Immunol* 10(6):423-34 also review this receptor superfamily. The use of TRAIL as an anti-tumor agent is discussed in Walczak et al. (1999) *Nature Medicine* 5:157-163.

SUMMARY OF THE INVENTION

Methods and composition are provided for modulating innate immunity by modulating activation of the TRAIL receptor. Signaling through the TRAIL-R inhibits the responsiveness of cells including dendritic cells, macrophages, and the like. The activity of these cells is increased or decreased by the administration of agents that inhibit or activate TRAIL-R signaling. In another embodiment of the invention, methods are provided for screening compounds or genes for activity in modulating innate immune responses by determining the effect of the agent on TRAIL-R signaling.

In another embodiment of the invention, a non-human animal model for screening and research purposes is provided, wherein the animal comprises a homozygous inactivation of the gene sequences encoding TRAIL-R. These animals appear to develop normally with an intact immune system, but have enhanced resistance to certain viruses and increased innate immune responses resulting from the absence of negative modulation by TRAIL-R signaling.

BRIEF DESCRIPTION OF THE DRAWINGS

FIG. 1A-1F. Targeted disruption of the mouse TRAIL receptor. (1a) A schematic map of the TRAIL-R genomic locus (top) and the targeting vector (bottom). The neomycin resistance cassette replaces a portion of the transmembrane domain and all of exon 6. A 5' Southern blot probe (1 kb XbaI fragment) is indicated. (1b) Confirmation of TRAIL-R locus targeting by Southern blot analysis of the transfected embryonic stem (ES) cells. Genomic DNA from ES cells was digested with BamHI, separated by electrophoresis, and hybridized with the radiolabeled 5' probe shown in (1a). Southern blot analysis detected a single 6.6 kb band for the wild-type allele and a 11 kb band for the knockout allele. (1c) PCR amplification of the heart TRAIL-R mRNAs from TRAIL-R$^{-/-}$ and TRAIL-R$^{+/-}$ mice was done as described in Materials and Methods. (1d) The TRAIL-R transcript from knockout mice was cloned and sequenced. Shown here is the abnormal junction between the 3$^{rd}$ and 7$^{th}$ exons formed in the TRAIL-R$^{-/-}$ heart mRNA, the normal TRAIL-R reading frame, and the predicted truncated protein sequence (*denotes termination codon). (1e) Wild-type and mutant transcripts were cloned into the pCI expression vector and transfected into 293T cells. Northern blot analysis (1e) showed a truncated TRAIL-R transcript from the knockout transcript construct. Western blot analysis (1f) showed normal TRAIL-R protein from the wild-type construct but no protein from the knockout construct.

FIG. 3. TRAIL-R deficiency does not affect immunity against *Salmonella typhimurium* or *Listeria monocytogenes* but increases survival to EMCV challenge. (a) TRAIL-R$^{-/-}$ and wild type (wt) littermates were infected by tail vein injection with 5×10$^5$ c.f.u. (colony forming units) of *L. monocytogenes*. Bacterial titers for the spleen and liver were determined at 3 and 5 days post infection. n=3 for each genotype/time point. (b) TRAIL-R$^{-/-}$ (n=3) and wild type (wt) littermates (n=7) were infected intraperitoneally with 1000 c.f.u. of *S. typhimurium* and monitored for indications of imminent death. (c) TRAIL-R deficient and wild type littermates were infected by the intraperitoneal route with 200 p.f.u. (plaque forming units) of EMCV. Animals were monitored for indications of imminent death.

FIG. 4A-4E. MCMV infected TRAIL-R$^{-/-}$ animals have decreased splenic viral titers and increased serum cytokine levels. TRAIL-R$^{-/-}$ (−/−) animals and wild type (wt) littermates were infected with 3×10$^5$ p.f.u. MCMV via the intraperitoneal (i.p.) route. (4a) Viral titers in the liver and spleen were determined at days 3 and 5 post infection. PFU values are given per 100 mg organ weight. Each time point represents 6 animals per genotype. The experiment has been repeated three times with similar results. (4b) NK cell lytic activity is unaffected by TRAIL-R deficiency. TRAIL-R$^{-/-}$ and wild type littermates were injected with either poly(I:C) or MCMV via i.p. route and NK cell lytic activity was assayed 24 hours later against $^{51}$Cr labeled YAC-1 targets. X axis corresponds to decreasing ratios of effector to target cells (E:T). (4c) Serum IL-12(p40) levels were measured by ELISA 24 hours post MCMV infection and IFN-γ levels were measured 36 hours post MCMV infection. (4d) Dendritic cells from MCMV infected TRAIL-R$^{-/-}$ animals display increased IL-12 production. Splenocytes from MCMV infected animals were isolated 24 hours post infection and sorted for CD11c expression. Cells were plated and cultured for 24 hours. IL-12(p40) in the culture medium was measured by ELISA. (4e) MCMV infected TRAIL-R$^{-/-}$ animals exhibit increased levels of type I interferons in their spleens and livers. Quantitative RT-PCR (done in triplicate for each sample) was performed on RNA from the spleens and livers of TRAIL-R$^{-/-}$ animals and wild-type littermates 4 and 8 hours post infection (For each genotype, n=2 for the 4 hour time point and n=3 for the 8 hour time point). The experiments have been repeated twice with similar results. The levels of α-interferon in the liver were too low to be detected. The interferon expression was normalized to γ-actin.

FIG. 5A-5C. Macrophages up-regulate TRAIL transcripts in response to stimulation with either *E. coli* LPS or Bacillus Calmette-Guerin (BCG) and TRAIL-R$^{-/-}$ macrophages display abnormal activation responses after BCG or LPS stimulation. (5a) Semi-quantitative RT-PCR was used to determine the levels of TRAIL and TRAIL-R transcripts in wild-type thioglycolate elicited peritoneal macrophages following stimulation with *E. coli* derived LPS or live BCG at the indicated time points. -RT: no reverse transcriptase. (5b) Thioglycolate elicited peritoneal macrophages from TRAIL-R$^{-/-}$ animals and wild-type littermates were stimulated with live BCG and stained for intracellular TNFα (12 hrs) and surface F4/80 and D$^b$ (24 hrs). The staining profiles at 6 hours post infection are equivalent to non-infected controls and are shown here for comparison. (5c) Cells were also stained for intracellular TNFα after treatment with *E. coli* LPS. The experiments were done three times with similar results.

DETAILED DESCRIPTION OF THE EMBODIMENTS

Figure 1A:
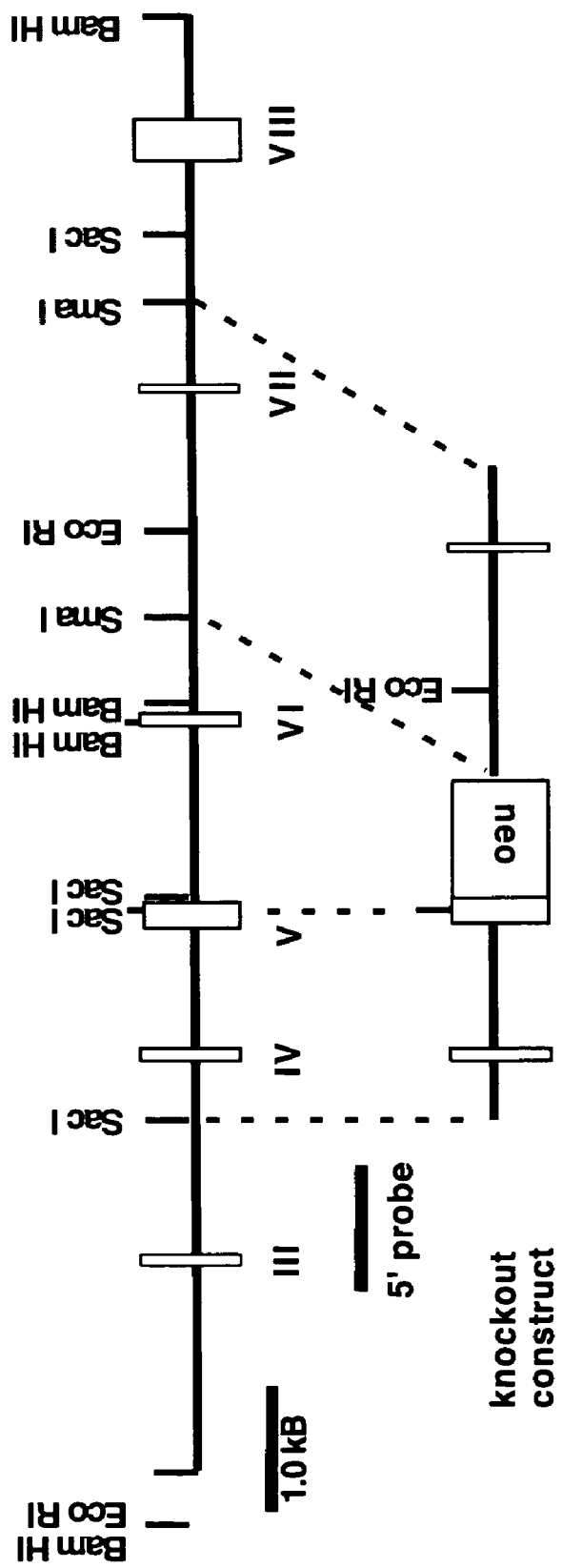

Methods and composition are provided for modulating innate immunity by modulating activation of the TRAIL receptor. Signaling through the TRAIL-R inhibits the responsiveness of cells including dendritic cells, macrophages, and the like. The activity of these cells is increased or decreased by the administration of agents that inhibit or activate TRAIL-R signaling.

In one embodiment of the invention, an animal model comprises a homozygous inactivation of the sequences encoding TRAIL-R is provided for the development of therapeutic agents and methods of modulation of innate immune responses, including responses to certain viruses, bacteria and autoimmune disorders.

In another embodiment of the invention, methods are provided for screening compounds and gene products for activity in mediating innate immune responses, by determining the effect of the agent on TRAIL-R signaling.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention, which will be limited only by the appended claims.

Innate Immune Responses. As used herein, the term innate immune response refers to non-antigen specific responses, for example the release of soluble effector compounds, non-specific phagocytosis performed by dendritic cells, macrophages, etc. It also refers to cellular changes that affect the abilities of cells to act as antigen presenting cells and/or modulate the antigen-specific adaptive immune response. Monocyte lineage cells mediate the initiation and progression of inflammation and other early immune responses by direct cytotoxicity, the secretion of soluble factors, and/or by regulating the adaptive immune response. These include the expression of adhesion molecules on monocyte derived cells and underlying vascular endothelium and the release of cytokines, chemokines, tissue-destructive metalloproteases and reactive oxygen species.

The mononuclear phagocyte system is comprised of both circulating and fixed populations of cells. The circulating component is the monocyte. Upon migration into tissues these are referred to as histiocytes or tissue macrophages. The major fixed macrophages include: sinusoidal lining cells of the spleen, lymph nodes, liver, and bone marrow; connective tissue histiocytes; mobile macrophages on serosal surfaces; alveolar macrophages within the lung; microglia in the nervous system; Kupffer cells in the liver; and mesangial macrophages within renal glomeruli.

Macrophages play a significant role in the host defense mechanism. These cells reside in various tissues and, along with dendritic cells, are among the first cells of any organ to be exposed to infectious agents and to become activated in response to an insult. Upon activation macrophages participate actively in the onset of inflammation by releasing pro-inflammatory cytokines and other bioactive molecules that amplify the initial inflammatory response. These inflammatory molecules include: members of the interleukin family, interferons, tumor necrosis factor, bioactive lipids (prostaglandins and leukotrienes), reactive oxygen intermediates (ROI) and reactive nitrogen intermediates (RNI) that exert cytotoxic effects against pathogens and tumor cells and activate other cells of the immune system. In addition, these cells are described as "professional" antigen presenting cells because of their capacity to effectively stimulate antigen-specific T cell activaiton. Activation of cells of the innate immune system by Gram-negative bacteria can be simulated in vitro by incubation of cells with lipopolysaccharide (LPS, a predominant glycolipid in the outer membrane of Gram-negative bacteria) alone or with LPS and IFN-γ acting as a pro-inflammatory cytokine. LPS or LPS with IFN-γ stimulate macrophage cells to an activated state, priming them for antimicrobial activity, increased killing of intracellular pathogens, and antigen processing and presentation to lymphocytes. These biological effects are mediated by up-regulating surface expression of several molecules, including MHC class II, and increasing release of nitric oxide (NO) and pro-inflammatory cytokines. Activation of the host immune system by viruses and other types of bacteria can also be simulated in vitro in a similar manner using other compounds such as poly(I:C), zymosan, LPS derived from Gram-positive bacteria, etc.

The term dendritic cell refers to any member of a diverse population of morphologically similar cell types found in lymphoid or non-lymphoid tissues. Dendritic cells are also referred to as "professional" antigen presenting cells and have a high capacity for activating T cells. Dendritic cells may be recognized by function, by cell surface phenotype, and/or by gene expression pattern. These cells are characterized by their distinctive morphology, high levels of surface MHC-class II expression and ability to present antigen to $CD4^+$ and/or $CD8^+$ T cells, particularly to naïve T cells (Steinman et al. (1991) *Ann. Rev. Immunol.* 9:271; incorporated herein by reference for its description of such cells). Among these cells are splenic dendritic cells, which produce cytokines including IL-12.

The cell surface of dendritic cells is unusual, with characteristic veil-like projections, and is characterized by expression of the cell surface markers CD11c and, when matured, MHC class II. Most DCs are negative for markers of other leukocyte lineages, including T cells, B cells, monocytes/macrophages, and granulocytes. Subpopulations of dendritic cells may also express additional markers including 33D1, CCR1, CCR2, CCR4, CCR5, CCR6, CCR7, CD1a-d, CD4, CD5, CD8alpha, CD9, CD11b, CD24, CD40, CD48, CD54, CD58, CD80, CD83, CD86, CD91, CD117, CD123 (IL3Rα), CD134, CD137, CD150, CD153, CD162, CXCR1, CXCR2, CXCR4, DCIR, DC-LAMP, DC-SIGN, DEC205, E-cadherin, Langerin, Mannose receptor, MARCO, TLR2, TLR3 TLR4, TLR5, TLR6, TLR9, and several lectins. The patterns of expression of these cell surface markers may vary along with the maturity of the dendritic cells, their tissue of origin, and/or their species of origin. Like macrophages, these cells can be stimulated in vitro to undergo cellular changes to effector type cells.

In some embodiments of the invention, TRAIL or other agents activating TRAIL-R signaling or its intracellular signaling pathway are administered to an individual to suppress the activation of monocytes, macrophages, dendritic cells, etc. Such activation may be associated with disease, e.g. pathogen challenge, inflammation, allergic reactions, etc., or may be part of normal biological homeostasis. In other embodiments; an inhibitor of the TRAIL-R signaling pathway is administered to enhance the activity of these cells.

Mammalian species that may require modulation of innate immune responses include canines; felines; equines; bovines; ovines; etc. and primates, particularly humans. Animal models, particularly small mammals, e.g. murine, lagomorpha, etc. may be used for experimental investigations. Animal models of interest include those involved with autoimmune disorders and the immune responses to infection and tumors.

TRAIL-Receptor. As used herein, the term TRAIL receptor, or TRAIL-R is intended to refer to the signaling human TRAIL receptors, TRAIL-R1 (DR4) and TRAIL-R2 (DR-5, TRICK2, KILLER), and homologs thereof, e.g. the mouse TRAIL-R. The sequence of the human TRAIL-R1 receptor is provided herein for convenience as SEQ ID NO:2; and the sequence of the human TNF-R1 receptor is provided as SEQ ID NO:3.

The ligand TRAIL may find use as an inhibitor of innate immune responses. The sequence of human TRAIL is provided herein for convenience as SEQ ID NO:1. Identification of non-human homologs is accomplished by conventional screening methods of DNA libraries or biological samples for DNA sequences having a high degree of similarity to known TRAIL sequences.

For various purposes the DNA sequences encoding TRAIL-R; TRAIL; etc. may be employed for synthesis of the complete protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as E. coli, B. subtilis, S. cerevisiae, or cells of a higher organism such as vertebrates, particularly mammals, e.g. COS 7 cells, may be used as the expression host cells. In some situations, it may be desirable to express a TRAIL gene in mammalian cells, where the protein will benefit from native folding and post-translational modifications.

The TRAIL-R peptides may also be prepared by synthesis. Various commercial synthetic apparatuses are available, for example, automated synthesizers by Applied Biosystems Inc., Foster City, Calif., Beckman, etc. By using synthesizers, naturally occurring amino acids may be substituted with unnatural amino acids, particularly diastereoisomers, side chains having different lengths or functionalities, and the like. The particular sequence and the manner of preparation will be determined by convenience, economics, purity required, and the like.

Other molecules that interact with the TRAIL receptors may be used in the subject methods. Such ligands will specifically bind to the extracellular domain of the receptor, and compete with the endogenous cognate ligand for binding. Ligands will also activate signaling through the death domain to activate apoptosis or other cellular changes, including inhibition of cellular activation. Candidate ligands are screened for their ability to meet these criteria. Assays to determine affinity and specificity of binding are known in the art, including competitive and non-competitive assays. Assays of interest include ELISA, RIA, flow cytometry, etc. Binding assays may use purified or semi-purified protein, or alternatively may use cells that express a TRAIL-R, e.g. cells transfected with an expression construct for a TRAIL-R, etc. As an example of a binding assay, purified receptor protein is bound to an insoluble support, e.g. microtiter plate, magnetic beads, etc. The candidate ligand and soluble, labeled TRAIL are added to the reaction, and the unbound components are then washed off. The ability of the candidate ligand to compete for receptor binding is determined by quantitation of bound, labeled TRAIL. A functional assay that detects apoptosis or other cellular responses may be used for confirmation.

Suitable ligands in addition to TRAIL and variants thereof include peptides, small organic molecules, peptidomimetics, antibodies, or the like. Antibodies may be polyclonal or monoclonal; intact or truncated, e.g. F(ab')$_2$, Fab, Fv; xenogeneic, allogeneic, syngeneic, or modified forms thereof, e.g. humanized, chimeric, etc.

Suitable antibodies for use as modulating agents are obtained by immunizing a host animal with peptides comprising all or a portion of a TRAIL receptor, etc. Suitable host animals include mouse, rat, sheep, goat, hamster, rabbit, etc. The origin of the protein immunogen may be mouse, human, rat, monkey, etc. The host animal will generally be a different species than the immunogen, e.g. mouse TRAIL-R used to immunize hamsters; human TRAIL-R to immunize mice, etc. Methods to generate monoclonal antibodies are well known in the art and need not be further elaborated.

In many cases, the ligand will be a polypeptide, e.g. TRAIL, a specifically binding antibody thereto or fragment thereof, etc., but other molecules that provide relatively high specificity and affinity may also be employed. Combinatorial libraries provide comnpounds other than oligopeptides that have the necessary binding characteristics. Generally, the affinity will be at least about $10^{-6}$, more usually about $10^{-8}$ M, i.e. binding affinities normally observed with specific monoclonal antibodies.

Other molecules that interact with intracellular components of the TRAIL-R signaling pathway may be used in the subject method. Such molecules will alter the function of proteins within the cell important in transmitting the TRAIL-R signal. These include, but are not limited to, membrane permeable pharmaceutical compounds and exogenously expressed gene products delivered by retroviral means, etc.

Animal Models

In one embodiment, the present invention provides a non-human animal comprising a homozygous deletion of a TRAIL-R gene. The animal of the invention is characterized by lacking a functional receptor protein, which may be truncated, mutated, substantially absent, etc. The generated non-human TRAIL-R knockout animal can be used as a model of a disease; for studying the role of innate immunity in immune responses; for testing the specificity of TRAIL associated tumor therapies; and the like.

The animals are made using techniques that result in "knocking out" of the genomic sequences for TRAIL-R, or introducing an altered form of the genetic sequence. These animals are made using a construct that includes complementary nucleotide sequence to the TRAIL-R gene, but which encode an inactivated or otherwise altered TRAIL-R gene. These manipulations are performed by insertion of DNA into the embryonic stem (ES) cells using microinjection or other techniques known to those skilled in the art such as electroporation, as described below. ES cells are selected on the basis of inactivating the gene encoding TRAIL-R and are used to create chimaeric animals, which are bred to obtain animals heterozygous for the defective gene. Animals that are heterozygous for the defective gene can also be obtained by breeding a normal animal with an animal that is homozygous for the defective TRAIL-R gene form. Animals lacking a functional TRAIL-R can be crossed with other transgenic or knockout animals, as described in the following examples.

Animals suitable for transgenic and knockout experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Methods for the culturing of ES cells and the subsequent production of knockout animals, the introduction of DNA into ES cells by a variety of methods such as electroporation, calcium phosphate/DNA precipitation, and direct injection are described in detail in Teratocarcinomas and embryonic stem cells, a practical approach, ed. E. J. Robertson, (IRL Press 1987), the teachings of which are incorporated herein. In cases involving sequence specific gene integration, a nucleic acid sequence for recombination with the TRAIL-R gene or sequences for controlling expression thereof also contains a gene encoding a marker such as neomycin resistance. Transfection is carried out by one of several methods described in detail in Lovell-Badge, in Teratocarcinomas and embryonic stem cells, a practical approach, ed. E. J. Robertson, (IRL Press 1987) or in Potter et al Proc. Natl. Acad. Sci. USA 81, 7161 (1984), including calcium phosphate/DNA precipitation, direct injection, and electroporation.

In these procedures, a number of ES cells, for example, $0.5 \times 10^6$, are plated into tissue culture dishes and transfected with a mixture of the linearized nucleic acid sequence and a neomycin resistance marker (Southern and Berg, J Mol. Appl. Gen. 1:327-341 (1982)) precipitated in the presence of lipofectin. DNA molecules introduced into ES cells can be integrated into the chromosome through the process of homologous recombination, described by Capecchi, (1989). The cells are fed with selection medium containing fetal bovine serum in DMEM supplemented with an antibiotic such as G418. Colonies of cells resistant to G418 are isolated using cloning rings and expanded. Selection of the desired clone of ES cells containing the mutated gene form is accomplished through one of several means. DNA is extracted from drug resistant clones and Southern blotting experiments using a gene specific nucleic acid sequence as a probe are used to identify those clones carrying the desired nucleic acid sequences. In some experiments, PCR methods are used to identify the clones of interest.

Direct injection of DNA results in a high efficiency of integration. Desired clones are identified through PCR of DNA prepared from pools of injected ES cells. Positive cells within the pools are identified by PCR subsequent to cell cloning (Zimmer and Gruss, Nature 338, 150-153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., Nature 338, 153-156 (1989) and Capecchi, (1989), the teachings of which are incorporated herein.

Naturally cycling or superovulated females mated with males are used to harvest embryos for the injection of ES cells containing the mutated gene form. Embryos of the appropriate age are recovered after successful mating. Embryos are flushed from the uterine horns of mated females and placed in Dulbecco's modified essential medium plus 10% calf serum for injection with ES cells. Approximately 10-20 ES cells are injected into blastocysts using a glass microneedle with an internal diameter of approximately 20 µm.

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

For screening, samples (1-2 cm of mouse tails) are removed from young animals. For larger animals, blood or other tissue can be used. To test for chimaerism in the homologous recombination events, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$. and $F_2$). Once the knockout animals are identified, lines are established by conventional breeding and used as the donors for tissue removal and implantation using standard techniques.

Animals expressing a mutated form of a gene or overexpressing a natural form of a gene by either "knock-in" technology or transgenesis may also be used.

The subject animals are useful for screening candidate therapeutic agents and treatment modalities. Through use of the subject animals or cells derived therefrom, one can identify ligands or substrates that affect the innate immune responses or TRAIL-R signaling of a host animal. Drug screening protocols may include a panel of animals, for example a test compound or combination of test compounds, and negative and/or positive controls, where the positive controls may be known immunosuppressive agents. Such panels may be treated in parallel, or the results of a screening assay may be compared to a reference database.

Depending on the particular assay, whole animals may be used, or cells derived therefrom. Cells may be freshly isolated from an animal, or may be immortalized in culture. Candidate therapies may be novel, or modifications of existing treatment options. For screening assays that use whole animals, a candidate agent, or treatment is applied to the subject animals. Typically, a group of animals is used as a negative, untreated or placebo-treated control, and a test group is treated with the candidate therapy. Generally a plurality of assays are run in parallel with different agent dose levels to obtain a differential response to the various dosages. The dosages and routes of administration are determined by the specific compound or treatment to be tested, and will depend on the specific formulation, stability of the candidate agent, response of the animal, etc.

The analysis may be directed towards determining effectiveness in prevention of disease induction, where the treatment is administered before infection or exposure to an activating agent. Alternatively, the analysis is directed toward regression of existing conditions, and the treatment is administered after initial onset of the disease, or establishment of moderate to severe disease. Frequently, treatment effective for prevention is also effective in regressing the disease.

In either case, after a period of time sufficient for the development or regression of the disease, the animals are assessed for impact of the treatment, by visual, histological, immunohistological, and/or other assays suitable for determining effectiveness of the treatment. The results may be expressed on a semi-quantitative or quantitative scale in order to provide a basis for statistical analysis of the results.

The term "agent" as used herein describes any molecule, e.g. protein or pharmaceutical, with the capability of affecting normal TRAIL-R signaling, including receptor expression, ligand-receptor interactions, and downstream signaling events. An agent or treatment is administered to an animal of the invention, or to cells derived therefrom. Pharmaceutical agents, antibodies, other proteins, etc. are of interest.

Compound Screening

Compound screening may be performed using a cellular interaction model, a genetically altered cell or animal, or purified proteins that provide for an interaction between TRAIL-R and ligands thereof. Cells of interest for screening include monocytes, macrophages, dendritic cells, and other cells involved in innate immune responses. These cells may express native TRAIL-R, or may be genetically altered to knockout the receptor, or express an exogenous TRAIL-R or mutated form of TRAIL-R. One can identify ligands or substrates that bind to, and/or modulate the interaction of receptor and ligand as well as substances that alter the signaling events downstream of TRAIL-R signaling.

For screening methods, it may not be necessary, or even desirable, to use the complete proteins for studying interactions. Soluble forms of the components, which lack the transmembrane domains, are of interest for in vitro screening. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site, or to minimize misfolding by substitution or deletion of one or more cysteine residues that are not necessary for function. Variants can be designed so as to retain or have enhanced biological activity of a particular region of the protein (e.g., a functional domain, transmembrane domain, etc.) Variants also include fragments of the polypeptides, particularly biologically active fragments and/or fragments corresponding to functional domains, which are sufficient for specific binding interactions. Fragments of interest may at least about 10 aa, at least about 15 aa in length, usually at least about 50 aa in length, and can be as long as 300 aa in length or longer.

Transgenic and knockout animals or cells derived therefrom are also used in compound screening. Compound screening identifies agents that modulate the function of cells involved in innate immune responses. Of particular interest are screening assays for agents that have a low toxicity for human cells. A wide variety of assays may be used for this purpose, including labeled in vitro protein-protein binding assays, functional assays for macrophage activation, immunoassays for protein binding, and the like. Knowledge of the 3-dimensional structure of the encoded protein, derived from crystallization of purified recombinant protein, could lead to the rational design of small drugs that specifically inhibit activity. These drugs may be directed at specific domains.

A candidate agent may be any molecule, e.g. protein or pharmaceutical, with the capability of altering the physiological function of innate immune responses. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Candidate agents also encompass numerous classes of proteins, including antibodies in intact, truncated, or otherwise modified forms.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of interfering with the binding between TRAIL-R and a ligand, as at least some of the compounds so identified are likely inhibitors. The binding assays usually involve contacting a cell or combination of cells or protein or combination of proteins with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89.

Certain screening methods involve screening for a compound that modulates the expression of TRAIL-R gene. Such methods generally involve conducting cell-based assays in which test compounds are contacted with one or more cells expressing a TRAIL-R gene and then detecting a decrease or increase in expression. Some assays are performed with cells that express endogenous TRAIL-R genes. Alternatively, some assays are performed with cells expressing native or modified TRAIL-R under the control of heterologous or mutated regulatory sequences.

Other screening methods involve screening for compounds that alter events downstream of TRAIL-R crosslinking. Such methods generally involve assaying for changes in cellular responses to TRAIL-R signaling following treatment with test compounds. Such assays include detection of changes in expression of cell surface markers and/or production of effector compounds such as ROI, RNI, and cytokines such as interleukins and interferons.

The level of expression or activity can be compared to a baseline value. The baseline value can be a value for a control sample or a statistical value that is representative of expression levels for a control population. Expression levels can also be determined for cells that do not express a TRAIL-R gene, as a negative control. Such cells generally are otherwise substantially genetically the same as the test cells. Various controls can be conducted to ensure that an observed activity is authentic including running parallel reactions with cells that lack the reporter construct or by not contacting a cell harboring the reporter construct with test compound. Compounds can also be further validated as described below.

Compounds that are initially identified by any of the foregoing screening methods can be further tested to validate the apparent activity. The basic format of such methods involves administering a lead compound identified during an initial screen to an animal that serves as a model for humans and then determining the initiation and/or progression of disease. The animal models utilized in validation studies generally are mammals. Specific examples of suitable animals include, but are not limited to, primates, mice, and rats.

Active test agents identified by the screening methods described herein that specifically modulate TRAIL-R signaling can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Pharmaceutical Formulations

As used herein, the term "treating" is used to refer to both prevention of disease, and treatment of pre-existing conditions. In the treatment of ongoing disease, the treatment stabilizes or reduces the undesirable clinical symptoms of the patient. Such treatment is desirably performed prior to complete loss of function in the affected tissues. The subject therapy may be administered before, or during the symptomatic stage of the disease, and in some cases after the symptomatic stage of the disease.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, injection into the cerebrospinal fluid, intracavity or direct injection in the demyelinating disease. Intrathecal administration maybe carried out through the use of an Ommaya reservoir, in accordance with known techniques. (F. Balis et al., Am J. Pediatr. Hematol. Oncol. 11, 74, 76 (1989).

The effective amount of a therapeutic composition to be given to a particular patient will depend on a variety of factors, several of which will be different from patient to patient. A competent clinician will be able to determine an effective amount of a therapeutic agent to administer to a patient to retard the harmful inflammation, or an effective amount of an imaging composition to administer to a patient to facilitate the diagnosis and visualization of demyelinated lesions. Dosage of the agent will depend on the treatment of the disease, route of administration, the nature of the therapeutics, sensitivity of the disease to the therapeutics, etc. Utilizing $LD_{50}$ animal data, and other information, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Imaging moieties are typically less toxic than cytotoxic moieties and may be administered in higher doses in some embodiments. Utilizing ordinary skill, the competent clinician will be able to optimize the dosage of a particular therapeutic or imaging composition in the course of routine clinical trials.

Typically the dosage will be 0.001 to 100 milligrams of conjugate per kilogram subject body weight. Relatively large doses, in the range of 0.1 to 10 mg per kilogram of patient body weight, may used for imaging conjugates with a relatively non-toxic imaging moiety. The amount utilized will depend on the sensitivity of the imaging method, and the relative toxicity of the imaging moiety.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the array" includes reference to one or more arrays and equivalents thereof known to those skilled in the art, and so forth. All technical and scientific terms used herein have the same meaning as commonly understood to one of ordinary skill in the art to which this invention belongs unless clearly indicated otherwise.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Generation of TRAIL-R$^{-/-}$ Mice.

Figure 1B:
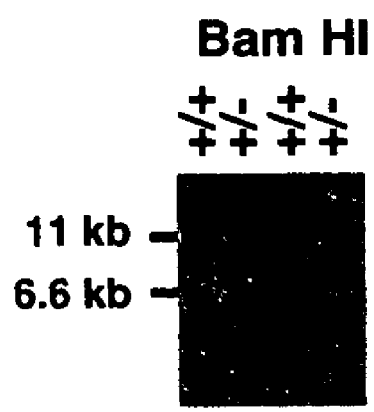

To assess the normal physiological function of the TRAIL receptor, TRAIL-R$^{-/-}$ mice were generated. The knockout construct replaced a portion of exon 5 (containing the transmembrane domain) and exon 6 with a neomycin gene cassette (FIG. 1a). Embryonic stem cells containing the desired homologous recombination were identified by Southern blot analysis using 5' and 3' probes and used to generate TRAIL-R heterozygous mice (FIG. 1b). TRAIL-R$^{+/-}$ mice were crossed to C57BL/6 for several generations and subsequently intercrossed to produce homozygous animals. TRAIL-R$^{-/-}$ mice were born at the expected Mendelian ratios and showed no gross developmental abnormalities.

Figure 1C:
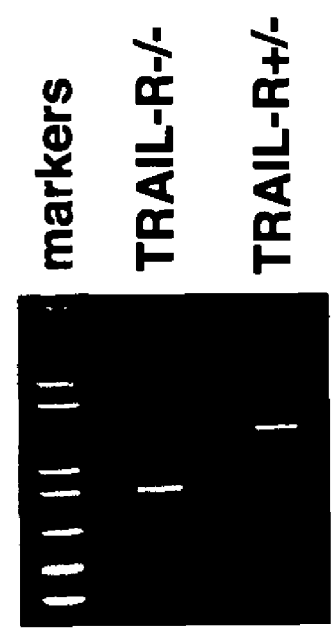

RT-PCR analysis was performed to determine if the TRAIL-R was indeed absent in TRAIL-R$^{-/-}$ mice. Direct protein analysis was not possible because none of the commercially available antibodies for human DR4 or DR5 cross-reacts with the mouse TRAIL-R protein. Furthermore, a rabbit polyclonal antibody generated against a bacterially expressed GST-TRAIL-R could only detect TRAIL-R in transiently transfected cells, but not the endogenous protein, presumably because of extremely low levels of endogenous TRAIL-R. RT-PCR analysis using TRAIL-R specific oligonucleotides showed the nearly complete absence of the transcript in the thymus of TRAIL-R$^{-/-}$ animals; however, a truncated product could be seen at low levels in other tissues (FIG. 1c).

Cloning and sequencing of this truncated transcript indicated that the mutation in the TRAIL-R locus resulted in mRNA splicing from exon 3 to exon 7, skipping exon 4 and introducing a frame shift and an early stop codon within exon 7 (FIG. 1d). The resulting predicted protein contains most of the extracellular domain of the TRAIL-R but lacks a transmembrane domain or any of the cytoplasmic tail. To determine if a stable protein could be encoded by this mutant sequence, constructs containing the coding region from either the wild type or mutant TRAIL-R transcripts were transfected into 293T cells.

Figure 1E:
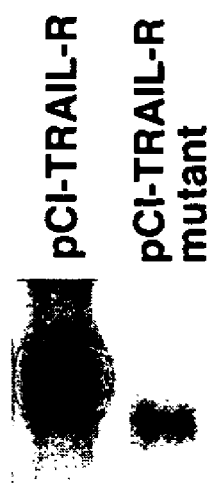
Figure 1F:
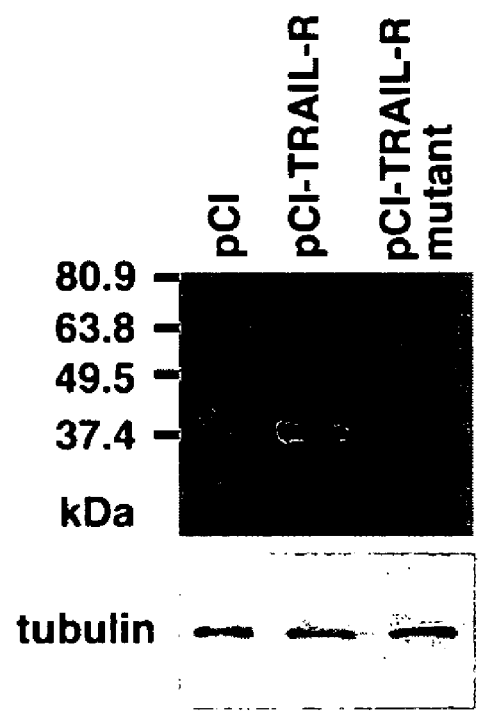

Consistent with the endogenous TRAIL-R transcript levels, Northern blot analysis showed lower mRNA expression of the mutant transcript in transfected cells compared to the level of the wild-type transcript in transfected cells (FIG. 1e). Western blot analysis using a TRAIL-R specific polyclonal antibody showed that while the wild-type construct produced TRAIL-R protein at the expected size, no protein was generated by the mutant construct (FIG. 1f). These data demonstrated that our targeted allele is indeed a null mutation. To remove neomycin from the gene locus, TRAIL-R$^{+/-}$ mice were crossed to CMV-Cre transgenic animals. No differences between animals with or without the neomycin cassette were observed and an identical mutant transcript is produced by the neomycin-deleted locus.

Normal Lymphocyte Populations and Negative Selection in TRAIL-R$^{-/-}$ Mice

Cells from the thymus, spleen, and lymph nodes of 5 to 12 week old TRAIL-R$^{-/-}$ animals and their littermate controls were isolated and analyzed by flow cytometry. Loss of TRAIL-R did not result in any changes of the T, B, macrophage, dendritic, or natural killer cell populations. The expected CD4 and CD8 ratios and normal activation markers (CD25, CD44, CD69, and CD62L) were found for the TRAIL-R$^{-/-}$ T cells. Aged TRAIL-R$^{-/-}$ animals (up to 45 weeks) also appeared normal and presented no evidence of abnormally activated cells compared to their wild-type littermates. In particular, aged TRAIL-R$^{-/-}$ animals did not develop lpr like symptoms, indicating that TRAIL-R does not play a similar role to Fas in lymphocyte homeostasis.

Figure 2:
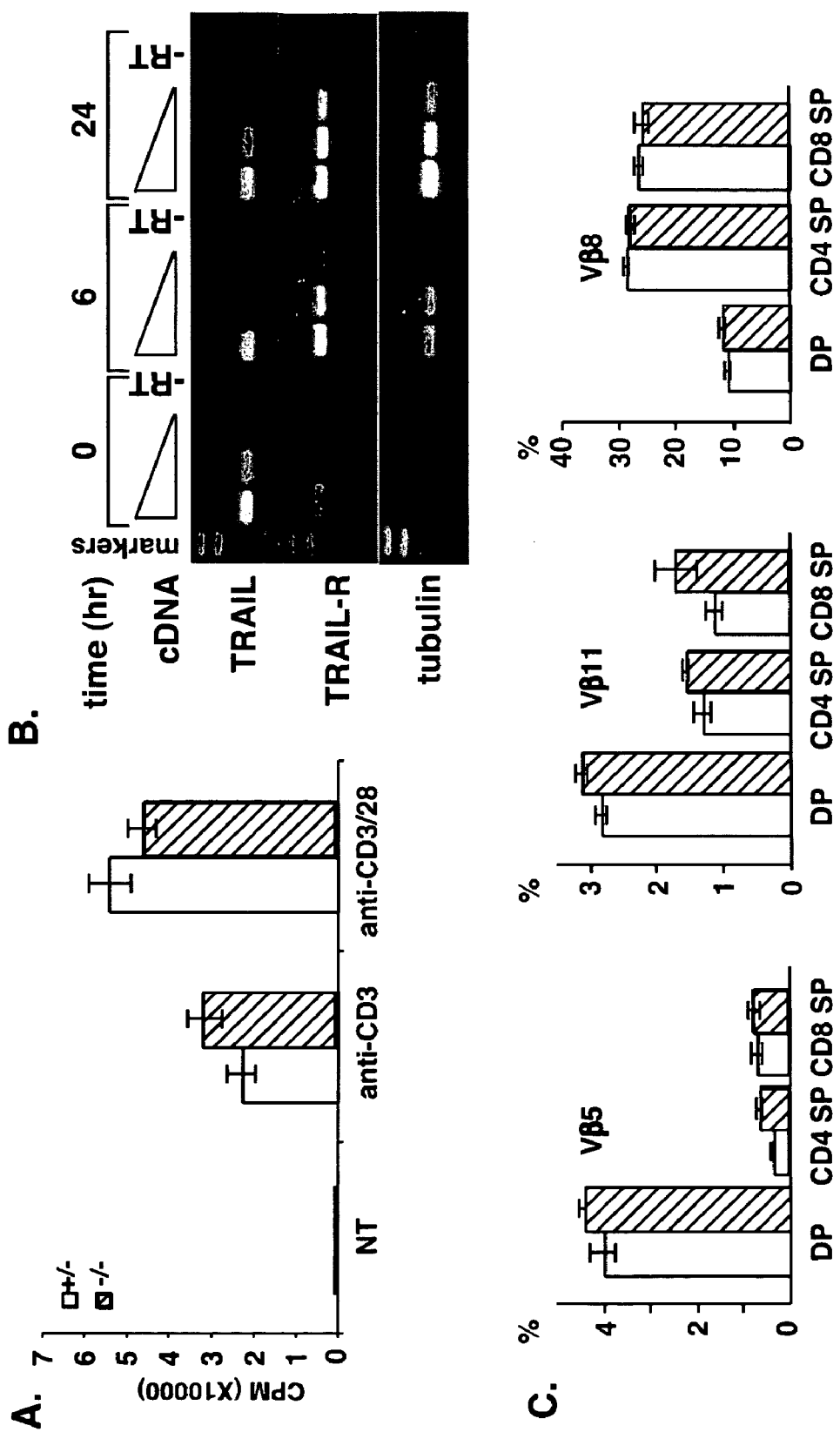
FIG. 2. T cells from TRAIL-R deficient mice proliferate normally and superantigen mediated thymic deletion is intact in TRAIL-R deficient mice. (a) Proliferation of lymphocytes from TRAIL-R deficient (−/−) and wild type littermate (+/−) animals was analyzed by thymidine incorporation after treatment with anti-CD3 or a combination of anti-CD3/anti-CD28 antibodies. NT denotes no treatment. (b) TRAIL and TRAIL-R transcripts from lymph node cells were analyzed by semi-quantitative RT-PCR after treatment with anti-CD3 and anti-CD28 antibodies for 6 and 24 hours. Tubulin was used as a control. -RT denotes no reverse transcriptase. (c) Mtv-9 superantigen mediated deletion was assayed in TRAIL-R mice backcrossed for 4 generations into the BALB/c background. Thymocytes from TRAIL-R deficient and wild type littermate controls were stained for CD4, CD8, and Vβ5, Vβ11, or Vβ8.

It has been reported that blocking TRAIL function by soluble DR5 protein led to enhanced anti-CD3 T cell proliferation. However, injection of soluble DR5 had no effect on proliferation of peptide-specific T cells. To see if loss of TRAIL-R leads to proliferation defects, we stimulated T cells from TRAIL-R$^{-/-}$ and wild-type littermates with anti-CD3 or a combination of anti-CD3 and anti-CD28 agonist antibodies. No significant alterations in T cell proliferation in the absence of TRAIL-R were found (FIG. 2a). Proliferation of T cells from wild-type animals activated in the presence and absence of exogenous recombinant TRAIL was also examined. Again, no significant difference was observed. Consistent with these data, and in contrast with studies using human T cells, semi-quantitative RT-PCR analysis of anti-CD3/CD28 treated wild-type T cells did not show any significant increase in TRAIL or TRAIL-R transcript levels following stimulation (FIG. 2b).

TRAIL deficient mice were reported to exhibit defective negative selection and increased thymocyte cellularity. Thymi from 5-8 week old TRAIL-R$^{-/-}$ animals, however, possessed normal thymocyte numbers (mutant thymocytes: 9.3±1.3×10$^7$, n=12; wild type thymocytes: 10.6±1.2×10$^7$, n=15) as well as normal CD4 and CD8 populations compared to wild-type littermate controls. To determine if superantigen induced negative selection was defective in our TRAIL-R$^{-/-}$ animals, we backcrossed the TRAIL-R null allele to the Balb/c background for four generations and examined mammary tumor virus (Mtv)-induced negative selection (FIG. 2c). Balb/c strain of mice are I-E$^d$ and carry Mtv-9 which encodes an endogenous superantigen capable of deleting $V_\beta 3$, $V_\beta 5$, and $V_\beta 11$ expressing T cells during negative selection. We examined the frequency of $V_\beta 5$ and $V_\beta 11$ in the thymi of seven-week old TRAIL-R$^{-/-}$ animals. As a control, $V_\beta 8^+$ T cell frequency was also assessed. As shown in FIG. 2C, there was a dramatic decrease in the frequencies of $V_\beta 5^+$ and $V_\beta 11^+$ but not $V_\beta 8^+$ cells following selection {between DP (CD4$^+$ CD8$^+$) and SP (CD4$^+$CD8$^-$ or CD4$^-$CD8$^+$) cells}. However, no differences between TRAIL-R$^{-/-}$ animals and their littermate controls were seen. These data argue against a significant role for TRAIL-R signaling during thymic negative selection. Consistent with this finding, a recent report showed that negative selection is normal in TRAIL-deficient animals.

TRAIL-R$^{-/-}$ Mice Show Normal Anti-bacterial Responses

The lack of defects in naive TRAIL-R deficient animals prompted us to examine the response of these animals to a variety of pathogen challenges. We first examined the response of TRAIL-R$^{-/-}$ animals to the Gram positive bacterium *Listeria monocytogenes*. Examination of spleen and liver titers three and five days post-infection from TRAIL-R deficient animals and wild-type littermates revealed similar bacterial titers (FIG. 3a). We also examined the survival of TRAIL-R$^{-/-}$ animals following infection with the Gram negative bacterium *Salmonella typhimurium*. Animals lacking TRAIL-R succumbed to the bacterial infection with the same kinetics as wild-type littermates (FIG. 3b). These data suggest that TRAIL-R signaling may not play a significant role in immunity against some types of bacteria.

TRAIL-R$^{-/-}$ Mice Have Enhanced Anti-viral Responses

Previous studies have suggested a role for TRAIL-R signaling during the immune response to viral infections. Others have shown that administration of a neutralizing TRAIL antibody leads to greater susceptibility to encephalomyocarditis virus (EMCV). We therefore examined the response of our TRAIL-R deficient animals to an EMCV challenge. Surprisingly, TRAIL-R deficient animals consistently displayed enhanced survival compared to littermate animals with a functional TRAIL-R (FIG. 3c). A ten-fold higher viral dose increased the rate at which all animals succumbed to infection and abrogated the difference in survival between wild type and TRAIL-R$^{-/-}$ animals.

Mice deficient for the p50 subunit of NK-κB are protected from a lethal EMCV challenge through enhanced apoptosis of virally infected cells which prevents viral spread. To determine if a similar mechanism accounted for the increased survival of TRAIL-R$^{-/-}$ mice, we generated fibroblasts from embryonic day 13.5 TRAIL-R deficient animals and wild-type littermates. Fibroblasts lacking TRAIL-R infected with various doses of EMCV displayed identical rates of death compared to TRAIL-R expressing cells. Consistent with this finding, viral titers in the hearts of TRAIL-R$^{-/-}$ animals were similar to their wild-type littermates 2 and 3 days post-challenge. Therefore, the enhanced survival of TRAIL-R deficient animals does not appear to be due to reduced virus induced apoptosis or viral spread.

Figure 4A:
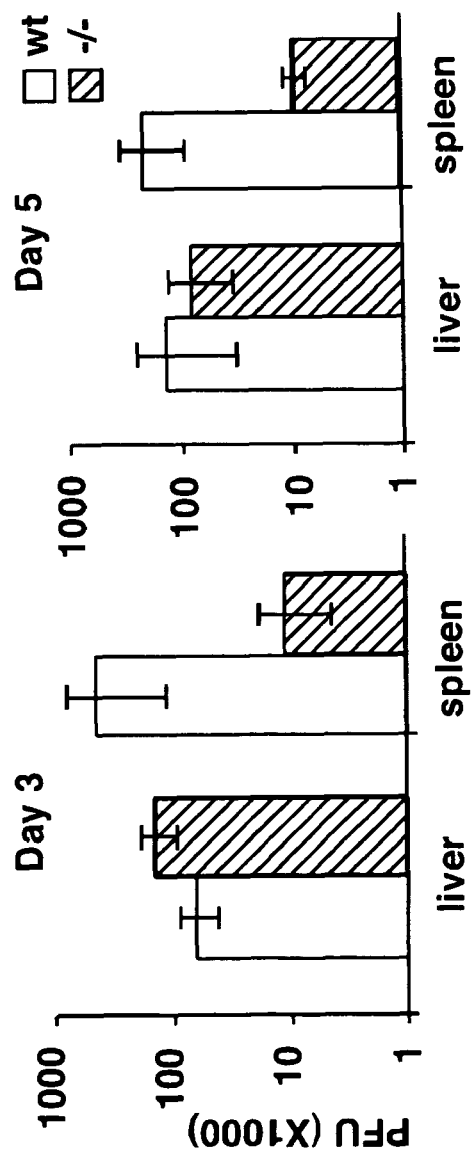

Natural killer cells are known to play an important role in the initial immune response that controls the spread of a spectrum of viral pathogens. It has been shown that NK cells express functional TRAIL on their surface following activating stimuli, and some cells become sensitive to TRAIL-R induced apoptosis following viral infection. The role of NK cells in the immune response to murine cytomegalovirus (MCMV) has been well characterized. In addition to perforin-mediated lysis of infected cells, NK cells secrete cytokines, including γ-interferon, that promote an antiviral state. To determine if TRAIL-R deficiency affected the responses to this virus, TRAIL-R$^{-/-}$ animals and wild type littermates in the B6 background were infected with MCMV (Smith strain) and viral titers were determined for the lungs, spleens, and livers. TRAIL-R deficient animals had unexpectedly lower viral loads in their spleens compared to control animals (FIG. 4a). Liver and lung viral titers were not significantly different between TRAIL-R deficient and wild-type animals, although liver titers were consistently slightly lower in the knockout animals. Differences in viral titers were observed as early as 3 days post infection with up to a 40-fold difference between TRAIL-R$^{-/-}$ animals and their littermate controls (FIG. 4a).

Figure 4B:
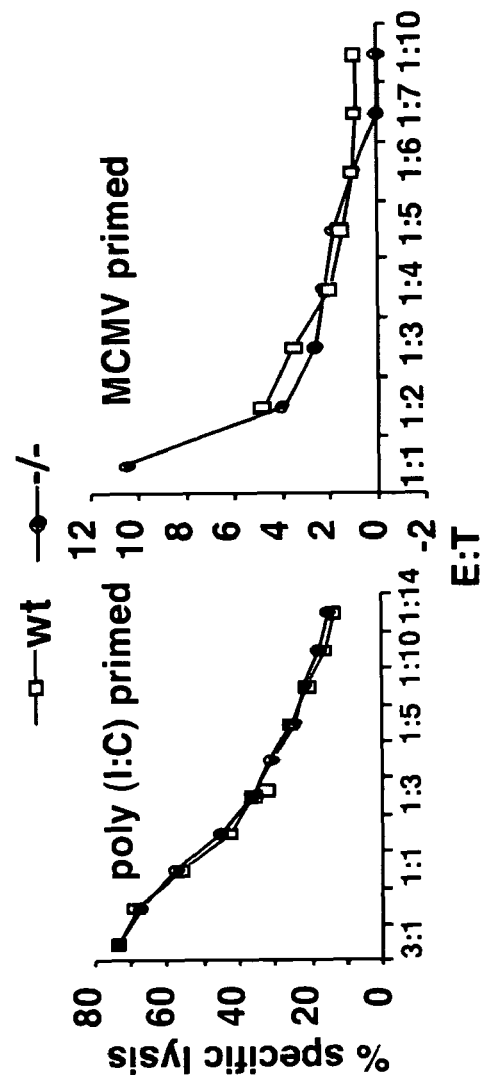

It has been shown previously that control of viral titers in the spleen is dependent on NK cell lytic activity. Therefore, we examined the lytic activity of NK cells lacking the TRAIL-R. Splenic NK cells were obtained from TRAIL-R deficient animals and wild type littermates following an intraperitoneal injection of poly(I:C). The NK cells from TRAIL-R knockout animals and control animals had identical lytic activity against chromium labeled YAC-1 target cells (FIG. 4b, left panel). Because poly(I:C) provides a very strong activating signal that might mask subtle deficiencies, we also examined NK cells from TRAIL-R$^{-/-}$ and wild-type littermate animals infected with MCMV. The lytic activity of splenic NK cells was also similar between knockout and wild-type animals 36 hours post-infection (FIG. 4b, right panel). These data indicate that the enhanced immunity displayed by TRAIL-R$^{-/-}$ animals is not due to enhanced NK cell lytic activity. The Perth strain of MCMV was shown recently to cause paralysis of dendritic cells and immune suppression as evidenced by down-regulation of class II MHC, CD80 and CD40 levels. To examine this issue, we stained CD11c$^+$/CD3$^-$ dendritic cells following MCMV (Smith strain) infection. Down regulation of class II MHC A protein and CD80 is modest but CD40 is significantly suppressed by the Smith strain of MCMV. However, no difference can be seen between TRAIL-R$^{-/-}$ and the wild type littermate dendritic cells (CD40 levels at day 5: wt: 50.46±2.86%, n=5, TRAIL-R$^{-/-}$: 55.9±4.46%, n=5; CD40 levels at day 7 post infection: wt: 19.2±2.37%, n=4, TRAIL-R$^{-/-}$ 20.7±3.2%, n=3). These data suggest that TRAIL-R has no effect on the modest paralysis of dendritic cells caused by the Smith strain of MCMV.

Cytokine secretion by a variety of cells following viral infection assists in the establishment of an antiviral state. In the context of an MCMV infection, early IL-12 production by dendritic cells induces IFN-γ production whose levels in the serum peak 36 hours post-infection. NK cells are a major producer of IFN-γ, which is necessary in the liver for MCMV immunity. Examination of serum cytokine levels at 24 hours post-infection revealed a nearly 10-fold increase in levels of the IL-12 p40 subunit in TRAIL-R$^{-/-}$ animals compared to wild-type littermates (FIG. 4c). Furthermore, serum levels of IFN-γ at 36 hours post infection were greatly elevated in TRAIL-R$^{-/-}$ animals compared to wild-type littermates (FIG. 4c). To examine directly the cells that produce IL-12, CD11c$^+$ dendritic cells and CD11b(Mac-1)$^+$ CD11c$^-$ macrophages were isolated from the spleens of MCMV infected animals 24 hours post-infection. Cells were then cultured for 24 hours and IL-12 levels in the culture medium assayed by ELISA. Consistent with our serum IL-12 data, dendritic cells from TRAIL-R deficient animals produced 8 fold more IL-12 than cells from control animals (FIG. 4d). No IL-12 production was detected in CD11b$^+$ macrophages. Therefore, enhanced cytokine production by dendritic cell accounts for the elevated IL-12 in the serum of knockout animals.

In addition to IL-12, IFN-α and IFN-β are induced early during viral infection and contribute to protection against MCMV. Assessment of the type-I interferon levels by quantitative RT-PCR at 4 and 8 hours post MCMV infection showed elevated levels of IFN-α (FIG. 4e) in the spleen of TRAIL-R$^{-/-}$ mice compared to wild-type littermates (the IFN-α level in the liver was below detection). IFN-β levels in the liver and spleen showed the same trend although the difference between TRAIL-R deficient and wild-type mice was not as dramatic (FIG. 4e). These data suggest that TRAIL-R signaling negatively regulates in vivo production of cytokines produced by innate immune cells.

TRAIL-R$^{-/-}$ Macrophages Display Enhanced Cytokine Production

Human monocytes and macrophages up-regulate TRAIL after stimulation. We examined TRAIL and TRAIL-R transcript levels in thioglycolate elicited murine peritoneal macrophages following stimulation with E. coli derived lipopolysaccharide (LPS). In contrast to anti-CD3/CD28 stimulated T cells, mouse macrophages rapidly upregulated TRAIL transcripts following activation (FIG. 5a). Exposure of these macrophages to the Mycobacterium bovis Bacillus Calmette-Guerin (BCG) also led to rapid up-regulation of TRAIL transcripts with similar kinetics to LPS (FIG.5a). In contrast, the levels of TRAIL-R did not change significantly with either stimulation.

We next examined the effects of TRAIL-R deficiency in the macrophage response to LPS or BCG stimulation. Following exposure to BCG or LPS, macrophages secrete TNFα. We first examined production of TNFα by intracellular cytokine staining. Intracellular cytokine staining of macrophages isolated from TRAIL-R$^{-/-}$ animals consistently revealed higher and more sustained levels of TNFα production compared to macrophages isolated from wild-type littermates following stimulation with BCG or LPS (FIG. 5b, right two panels). In addition to TNFα production, BCG, but not LPS, causes down-regulation of the surface expression of the F4/80 macrophage specific antigen and class I major histocompatibility complex (MHC). Down-regulation of F4/80 and D$^b$ class I MHC cell surface expression is less pronounced in TRAIL-R$^{-/-}$ cells (FIG. 5b, left two panels). The function of F4/80 remains unclear, but studies using blocking antibodies suggest F4/80 enhances macrophage cytokine secretion and its down-regulation may be a mechanism for shutting off cytokine production. Therefore, increased F4/80 expression in TRAIL-R$^{-/-}$ cells is consistent with the increased TNFα production. The cause of D$^b$ down-regulation by BCG is also unclear, but may represent an immunosuppressive effect of BCG. Taken together, these data suggest that TRAIL-R is a regulator of TNFα production as well as the overall macrophage activation state.

Figure 6:
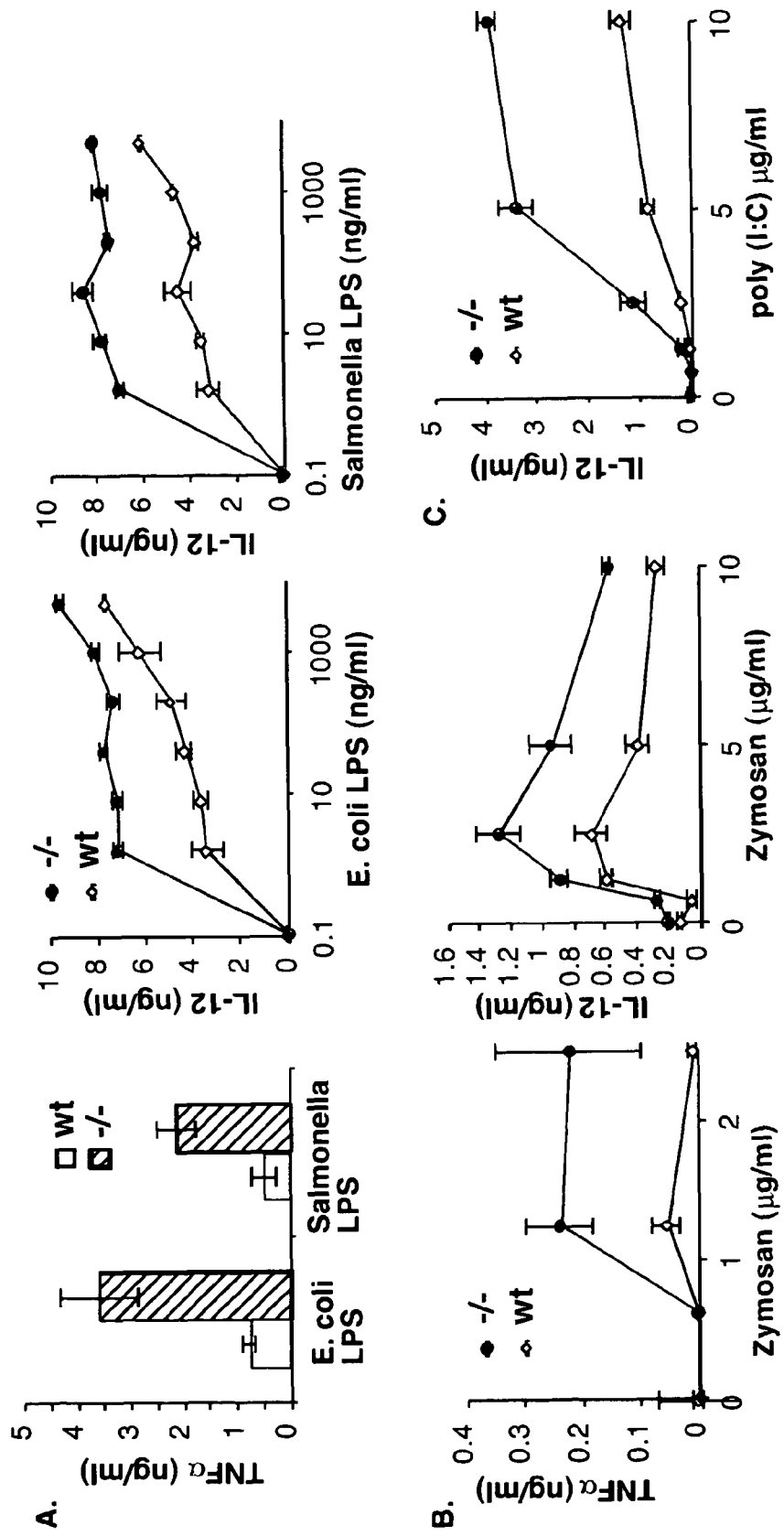
FIG. 6. Enhanced production of IL-12(p40) and TNFα in response to Toll-like receptor stimuli. (a-c) Thioglycolate elicited peritoneal macrophages from TRAIL-R$^{-/-}$ (−/−) and +/− or +/+ (wt) littermates were treated with titrated doses of various TLR specific stimulants. IL-12(p40) production was measured 24 hours post-treatment. TNFα was measured 6 hours post-treatment. These experiments have been repeated at least three times with similar results.

The Toll-like receptors (TLRs) recognize conserved motifs found on many microorganisms and represent the primary means by which macrophages and other cells of the innate immune system to recognize pathogens. Since LPS and BCG are known to activate macrophages through TLR4 and 2, respectively, we examined the response of macrophages to other TLR stimuli. Macrophages derived from TRAIL-R$^{-/-}$ animals and wild-type littermates were treated with LPS from *E. coli* and *Salmonella*, Zymosan A, and poly (I-C). In response to both forms of LPS, TRAIL-R$^{-/-}$ macrophages produced greater TNFα and IL-12 than wild-type macrophages (FIG. 6a). The same was true after stimulation with zymosan (FIG. 6b). TRAIL-R$^{-/-}$ macrophages also produced more IL-12 in response to poly (I:C) (FIG. 6c).

Figure 7:
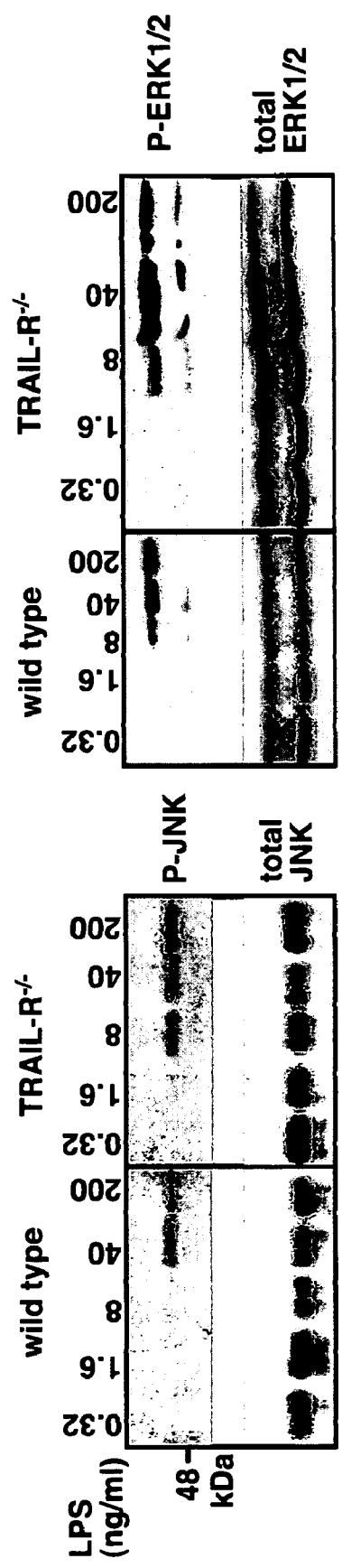
FIG. 7. Analysis of JNK and ERK1/2 activation in peritoneal macrophages from TRAIL-R$^{-/-}$ mice. Thioglycolate elicited peritoneal macrophages from TRAIL-R$^{-/-}$ and wild-type littermate controls were treated with 5 fold dilutions of *E. coli* LPS for 10 minutes. Cell lysates were separated on a 10% SDS-PAGE gel and transferred to nitrocellulose. Blots were probed with the indicated antibodies.

Recognition of pathogens by Toll-like receptors leads to a rapid defensive response. This response is mediated through activation of both MAP kinases as well as NF-κB. We examined these pathways following LPS stimulation to determine if TRAIL-R deficiency affected TLR downstream signaling events. To examine NF-κB activation, we analyzed levels of IκB-α, which sequesters NF-κB in the cytoplasm in a transcriptionally inactive complex. Activation of this pathway leads to phosphorylation and degradation of IκB-α, permitting the translocation of NF-κB to the nucleus and activation of transcriptional targets. Western blot analysis of IκB-α showed that macrophages from TRAIL-R$^{-/-}$ animals and wild-type littermates displayed similar kinetics of IκB-α phosphorylation and degradation during the first hour following LPS stimulation, indicating that TRAIL-R deficiency did not affect the initial activation of NF-κB. However, preliminary data indicates TRAIL-R signaling may be involved in the later stages of NF-κB regulation. We next examined activation of MAP kinases by examining phosphorylation of ERK1/2 and JNK. TRAIL-R deficient macrophages consistently showed slightly higher and more sustained levels of JNK phosphorylation following treatment with LPS. However, ERK1/2 was phosphorylated at similar levels in TRAIL-R$^{-/-}$ and wild type macrophages (FIG. 7). These data are consistent with the delayed time course of TRAIL up-regulation (4 hours post LPS stimulation, see above) and suggest that TRAIL-R primarily impacts late signaling events downstream of Toll-like receptors.

The vast majority of studies of TRAIL-R function have examined its abilities to induce apoptosis preferentially in transformed cells. The present data now demonstrates the importance of TRAIL-R signaling in the proximal response of the immune system to pathogen challenge.

Similar to TRAIL$^{-/-}$ mice, examination of unchallenged TRAIL-R$^{-/-}$ mice did not reveal any abnormalities in their resting immune cell populations, indicating that TRAIL-R does not play an essential, non-redundant role in the development of the immune system. In addition, lymphocyte homeostasis appears unperturbed, even in aged animals. It is interesting to note that, unlike mutation in the related family member Fas, TRAIL-R deficiency does not lead to lymphoproliferative conditions or the development of an abnormal B220$^+$/Thy1$^+$ T cell population. It has been shown previously that loss of TNF receptor in the lpr background can enhance the lymphoproliferative phenotype even though TNF-RI$^{-/-}$ animals display normal peripheral deletion. It remains to be seen whether compound deficiency in Fas and TRAIL-R would have any synergistic effects on lymphocyte homeostasis.

Examination of the lymphocyte populations from TRAIL-R deficient animals has revealed some differences with previous studies using either TRAIL deficient animals or TRAIL blocking antibodies. It has been reported that TRAIL deficiency leads to defects in negative selection, including defective endogenous superantigen deletion of certain thymocyte subsets. However, our TRAIL-R$^{-/-}$ animals display no such alterations when compared to wild-type littermates using the same model of endogenous superantigen deletion. We have been unable to show significant alterations in T cell proliferation following the addition of exogenous recombinant TRAIL. Furthermore, TRAIL-R loss in T cells does not significantly affect proliferation following TCR/CD28 ligation.

The normal lymphocyte homeostasis observed in our TRAIL-R deficient animals led us to examine TRAIL-R function in the context of an immune response to several bacterial and viral pathogens. While TRAIL-R loss had no effect on *L. monocytogenes* or *S. typhimurium* infection, it did have a significant protective effect in the context of both EMCV and MCMV infections. In the case of EMCV, loss of TRAIL-R conferred significantly enhanced survival against a lethal infection. The mechanism of this protection is unclear, but it likely does not involve virally induced apoptosis of infected cells or viral reproduction and spread to the heart, one of the main target organs.

In response to MCMV infection, TRAIL-R$^{-/-}$ animals had enhanced anti-viral responses, which led to lower viral titers in the spleens of knockout animals. NK cell lytic activity has been shown to be essential for viral clearance from the spleen. However, no increase in lytic activity was found in the TRAIL-R$^{-/-}$ NK cells, although more TRAIL-R$^{-/-}$ splenic NK cells expressed the CD69 activation marker. Analysis of cytokine production in knockout animals revealed elevated levels of IL-12 and IFN-γ in the serum compared to control animals. In addition, knockout animals displayed higher levels of type I interferons in the spleen, suggesting that enhanced cytokine production contributes to the increased clearance of MCMV from the spleens of knockout animals. We also examined splenic dendritic cells which have been identified as the major producer of IL-12 during an MCMV infection. Consistent with our serum cytokine data, dendritic cells derived from MCMV infected TRAIL-R$^{-/-}$ animals showed elevated production of IL-12 compared to dendritic cells from wild-type littermates. These data demonstrate that TRAIL-R negatively regulates the innate immune system.

Studies of TRAIL-R$^{-/-}$ macrophages further confirm the notion that TRAIL-R is a negative regulator of innate immunity. Challenge of TRAIL-R deficient macrophages ex vivo with live BCG resulted in enhanced TNFα production compared to TRAIL-R expressing cells without any effect on the cell viability. In addition, TRAIL-R$^{-/-}$ macrophages displayed enhanced cytokine production following a variety of TLR stimulants, including LPS, zymosan, and poly (I:C). Preliminary studies using CpG, however, suggest that not all TLR stimuli are regulated by the TRAIL-R.

Toll-like receptor ligation results in the activation of both MAP kinase pathways as well as the transcription factor NF-κB. Examination of these signaling pathways in TRAIL-R deficient macrophages following LPS stimulation indicates that while JNK activation is slightly elevated, early NF-κB and ERK activation are normal. Our observation that TRAIL is not up-regulated until 4 hours after LPS treatment suggests that TRAIL-R primarily impacts the later events following TLR signaling. The mechanism by which TRAIL-R interacts with the TLR signaling pathways and downstream events remains unclear.

In summary, the data presented here define a role for TRAIL-R signaling independent of its abilities to initiate apoptosis in sensitive cells. Using mice deficient for TRAIL-R, we have shown that TRAIL-R signaling contributes to the negative regulation of cytokine production in macrophages and dendritic cells in the context of both ex vivo and in vivo challenges. These data identify TRAIL-R as a dual-function receptor that not only signals apoptosis but also acts to inhibit the initiation of an immune response.

What is claimed is:

1. A method of enhancing an immune response, the method comprising:
   (i) contacting mammalian macrophages with an effective dose of an agent that inhibits tumor necrosis factor related apoptosis inducing ligand receptor (TRAIL-R), wherein the agent is selected from a blocking antibody specific for TRAIL and a blocking antibody specific for TRAIL-R; and
   (ii) contacting the mammalian macrophages with an infectious agent, wherein following said contacting of the mammalian macrophages with the infectious agent, the immune response is enhanced by mammalian macrophages having increased release of at least one cytokine selected from tumor necrosis factor alpha (TNFα), interleukin 12 (IL-12) and interferon alpha (IFN-α).

2. The method of claim 1, wherein said mammalian macrophages are contacted in vitro with the agent and the infectious agent.

3. The method of claim 1, wherein said mammalian macrophages are contacted in vivo with the agent and the infectious agent.

4. The method of claim 3, wherein the mammalian macrophages are present in a mouse.

5. The method of claim 3, wherein the mammalian macrophages are present in a human.

6. The method of claim 1, wherein the infectious agent is a virus.

7. A method of enhancing an immune response, the method comprising:
   (i) contacting mammalian dendritic cells with an effective dose of an agent that inhibits tumor necrosis factor related apoptosis inducing ligand receptor (TRAIL-R), wherein the agent is selected from a blocking antibody specific for TRAIL and a blocking antibody specific for TRAIL-R; and
   (ii) contacting the mammalian dendritic cells with an infectious agent, wherein following said contacting of the mammalian dendritic cells with the infectious agent, the immune response is enhanced by mammalian dendritic cells having increased release of interleukin 12 (IL-12).

8. The method of claim 7, wherein the infectious agent is a virus.

* * * * *

SEQUENCE LISTING

<160> NUMBER OF SEQ ID NOS: 6

<210> SEQ ID NO 1
<211> LENGTH: 1769
<212> TYPE: DNA
<213> ORGANISM: H. sapiens
<220> FEATURE:
<221> NAME/KEY: CDS
<222> LOCATION: (88)...(933)
<223> OTHER INFORMATION: Human TRAIL Coding Sequence

<400> SEQUENCE: 1

```
cctcactgac tataaagaa tagagaagga agggcttcag tgaccggctg cctggctgac         60
ttacagcagt cagactctga caggatc atg gct atg atg gag gtc cag ggg gga      114
                                Met Ala Met Met Glu Val Gln Gly Gly
                                 1               5 ccc agc ctg gga cag acc tgc gtg ctg atc gtg atc ttc aca gtg ctc        162
Pro Ser Leu Gly Gln Thr Cys Val Leu Ile Val Ile Phe Thr Val Leu
 10              15                  20                  25 ctg cag tct ctc tgt gtg gct gta act tac gtg tac ttt acc aac gag        210
Leu Gln Ser Leu Cys Val Ala Val Thr Tyr Val Tyr Phe Thr Asn Glu
             30                  35                  40 ctg aag cag atg cag gac aag tac tcc aaa agt ggc att gct tgt ttc        258
Leu Lys Gln Met Gln Asp Lys Tyr Ser Lys Ser Gly Ile Ala Cys Phe
         45                  50                  55 tta aaa gaa gat gac agt tat tgg gac ccc aat gac gaa gag agt atg        306
Leu Lys Glu Asp Asp Ser Tyr Trp Asp Pro Asn Asp Glu Glu Ser Met
     60                  65                  70 aac agc ccc tgc tgg caa gtc aag tgg caa ctc cgt cag ctc gtt aga        354
Asn Ser Pro Cys Trp Gln Val Lys Trp Gln Leu Arg Gln Leu Val Arg
 75                  80                  85 aag atg att ttg aga acc tct gag gaa acc att tct aca gtt caa gaa        402
Lys Met Ile Leu Arg Thr Ser Glu Glu Thr Ile Ser Thr Val Gln Glu
 90                  95                 100                 105 aag caa caa aat att tct ccc cta gtg aga gaa aga ggt cct cag aga        450
Lys Gln Gln Asn Ile Ser Pro Leu Val Arg Glu Arg Gly Pro Gln Arg
             110                 115                 120 gta gca gct cac ata act ggg acc aga gga aga agc aac aca ttg tct        498
Val Ala Ala His Ile Thr Gly Thr Arg Gly Arg Ser Asn Thr Leu Ser
         125                 130                 135 tct cca aac tcc aag aat gaa aag gct ctg ggc cgc aaa ata aac tcc        546
Ser Pro Asn Ser Lys Asn Glu Lys Ala Leu Gly Arg Lys Ile Asn Ser
     140                 145                 150 tgg gaa tca tca agg agt ggg cat tca ttc ctg agc aac ttg cac ttg        594
Trp Glu Ser Ser Arg Ser Gly His Ser Phe Leu Ser Asn Leu His Leu
 155                 160                 165 agg aat ggt gaa ctg gtc atc cat gaa aaa ggg ttt tac tac atc tat        642
Arg Asn Gly Glu Leu Val Ile His Glu Lys Gly Phe Tyr Tyr Ile Tyr
170                  175                 180                 185 tcc caa aca tac ttt cga ttt cag gag gaa ata aaa gaa aac aca aag        690
Ser Gln Thr Tyr Phe Arg Phe Gln Glu Glu Ile Lys Glu Asn Thr Lys
             190                 195                 200 aac gac aaa caa atg gtc caa tat att tac aaa tac aca agt tat cct        738
Asn Asp Lys Gln Met Val Gln Tyr Ile Tyr Lys Tyr Thr Ser Tyr Pro
         205                 210                 215 gac cct ata ttg ttg atg aaa agt gct aga aat agt tgt tgg tct aaa        786
Asp Pro Ile Leu Leu Met Lys Ser Ala Arg Asn Ser Cys Trp Ser Lys
     220                 225                 230
```

```
gat gca gaa tat gga ctc tat tcc atc tat caa ggg gga ata ttt gag    834
Asp Ala Glu Tyr Gly Leu Tyr Ser Ile Tyr Gln Gly Gly Ile Phe Glu
    235                 240                 245 ctt aag gaa aat gac aga att ttt gtt tct gta aca aat gag cac ttg    882
Leu Lys Glu Asn Asp Arg Ile Phe Val Ser Val Thr Asn Glu His Leu
250                 255                 260                 265 ata gac atg gac cat gaa gcc agt ttc ttc ggg gcc ttt tta gtt ggc    930
Ile Asp Met Asp His Glu Ala Ser Phe Phe Gly Ala Phe Leu Val Gly
                270                 275                 280 taa ctgacctgga aagaaaaagc aataacctca aagtgactat tcagttttca         983
ggatgataca ctatgaagat gtttcaaaaa atctgaccaa acaaacaaa cagaaaacag  1043 aaaacaaaaa aacctctatg caatctgagt agagcagcca caaccaaaaa attctacaac 1103 acacactgtt ctgaaagtga ctcacttatc ccaagaaaat gaaattgctg aaagatcttt 1163 caggactcta cctcatatca gtttgctagc agaaatctag aagactgtca gcttccaaac 1223 attaatgcaa tggttaacat cttctgtctt tataatctac tccttgtaaa gactgtagaa 1283 gaaagcgcaa caatccatct ctcaagtagt gtatcacagt agtagcctcc aggtttcctt 1343 aagggacaac atccttaagt caaagagag aagaggcacc actaaaagat cgcagtttgc 1403 ctggtgcagt ggctcacacc tgtaatccca cattttggg aacccaaggt gggtagatca 1463 cgagatcaag agatcaagac catagtgacc aacatagtga aacccatct ctactgaaag 1523 tgcaaaaatt agctgggtgt gttggcacat gcctgtagtc ccagctactt gagaggctga 1583 ggcaggagaa tcgtttgaac ccgggaggca gaggttgcag tgtggtgaga tcatgccact 1643 acactccagc ctggcgacag agcgagactt ggtttcaaaa aaaaaaaaa aaaaaaactt 1703 cagtaagtac gtgttatttt tttcaataaa attctattac agtatgtcaa aaaaaaaaa 1763 aaaaaa                                                            1769

<210> SEQ ID NO 2
<211> LENGTH: 281
<212> TYPE: PRT
<213> ORGANISM: H. sapiens

<400> SEQUENCE: 2

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160
```

```
His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
        180                 185                 190

Gln Glu Glu Ile Lys Glu Asn Thr Lys Asn Asp Lys Gln Met Val Gln
                195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 3
<211> LENGTH: 1407
<212> TYPE: DNA
<213> ORGANISM: H. sapiens
<220> FEATURE:
<221> NAME/KEY: CDS
<222> LOCATION: (1)...(1407)
<223> OTHER INFORMATION: Human TRAIL Receptor Coding Sequence

<400> SEQUENCE: 3 atg gcg cca cca cca gct aga gta cat cta ggt gcg ttc ctg gca gtg      48
Met Ala Pro Pro Pro Ala Arg Val His Leu Gly Ala Phe Leu Ala Val
1               5                   10                  15 act ccg aat ccc ggg agc gca gcg agt ggg aca gag gca gcc gcg gcc      96
Thr Pro Asn Pro Gly Ser Ala Ala Ser Gly Thr Glu Ala Ala Ala Ala
            20                  25                  30 aca ccc agc aaa gtg tgg ggc tct tcc gcg ggg agg att gaa cca cga     144
Thr Pro Ser Lys Val Trp Gly Ser Ser Ala Gly Arg Ile Glu Pro Arg
        35                  40                  45 ggc ggg ggc cga gga gcg ctc cct acc tcc atg gga cag cac gga ccc     192
Gly Gly Gly Arg Gly Ala Leu Pro Thr Ser Met Gly Gln His Gly Pro
    50                  55                  60 agt gcc cgg gcc cgg gca ggg cgc gcc cca gga ccc agg ccg gcg cgg     240
Ser Ala Arg Ala Arg Ala Gly Arg Ala Pro Gly Pro Arg Pro Ala Arg
65                  70                  75                  80 gaa gcc agc cct cgg ctc cgg gtc cac aag acc ttc aag ttt gtc gtc     288
Glu Ala Ser Pro Arg Leu Arg Val His Lys Thr Phe Lys Phe Val Val
                85                  90                  95 gtc ggg gtc ctg ctg cag gtc gta cct agc tca gct gca acc atc aaa     336
Val Gly Val Leu Leu Gln Val Val Pro Ser Ser Ala Ala Thr Ile Lys
            100                 105                 110 ctt cat gat caa tca att ggc aca cag caa tgg gaa cat agc cct ttg     384
Leu His Asp Gln Ser Ile Gly Thr Gln Gln Trp Glu His Ser Pro Leu
        115                 120                 125 gga gag ttg tgt cca cca gga tct cat aga tca gaa cgt cct gga gcc     432
Gly Glu Leu Cys Pro Pro Gly Ser His Arg Ser Glu Arg Pro Gly Ala
    130                 135                 140 tgt aac cgg tgc aca gag ggt gtg ggt tac acc aat gct tcc aac aat     480
Cys Asn Arg Cys Thr Glu Gly Val Gly Tyr Thr Asn Ala Ser Asn Asn
145                 150                 155                 160 ttg ttt gct tgc ctc cca tgt aca gct tgt aaa tca gat gaa gaa gag     528
Leu Phe Ala Cys Leu Pro Cys Thr Ala Cys Lys Ser Asp Glu Glu Glu
                165                 170                 175
```

```
                                                                                  -continued aga agt ccc tgc acc acg acc agg aac aca gca tgt cag tgc aaa cca                       576
Arg Ser Pro Cys Thr Thr Thr Arg Asn Thr Ala Cys Gln Cys Lys Pro
        180                 185                 190 gga act ttc cgg aat gac aat tct gct gag atg tgc cgg aag tgc agc                       624
Gly Thr Phe Arg Asn Asp Asn Ser Ala Glu Met Cys Arg Lys Cys Ser
    195                 200                 205 aca ggg tgc ccc aga ggg atg gtc aag gtc aag gat tgt acg ccc tgg                       672
Thr Gly Cys Pro Arg Gly Met Val Lys Val Lys Asp Cys Thr Pro Trp
210                 215                 220 agt gac atc gag tgt gtc cac aaa gaa tca ggc aat gga cat aat ata                       720
Ser Asp Ile Glu Cys Val His Lys Glu Ser Gly Asn Gly His Asn Ile
225                 230                 235                 240 tgg gtg att ttg gtt gtg act ttg gtt gtt ccg ttg ctg ttg gtg gct                       768
Trp Val Ile Leu Val Val Thr Leu Val Val Pro Leu Leu Leu Val Ala
                245                 250                 255 gtg ctg att gtc tgt tgt tgc atc ggc tca ggt tgt gga ggg gac ccc                       816
Val Leu Ile Val Cys Cys Cys Ile Gly Ser Gly Cys Gly Gly Asp Pro
            260                 265                 270 aag tgc atg gac agg gtg tgt ttc tgg cgc ttg ggt ctc cta cga ggg                       864
Lys Cys Met Asp Arg Val Cys Phe Trp Arg Leu Gly Leu Leu Arg Gly
        275                 280                 285 cct ggg gct gag gac aat gct cac aac gag att ctg agc aac gca gac                       912
Pro Gly Ala Glu Asp Asn Ala His Asn Glu Ile Leu Ser Asn Ala Asp
    290                 295                 300 tcg ctg tcc act ttc gtc tct gag cag caa atg gaa agc cag gag ccg                       960
Ser Leu Ser Thr Phe Val Ser Glu Gln Gln Met Glu Ser Gln Glu Pro
305                 310                 315                 320 gca gat ttg aca ggt gtc act gta cag tcc cca ggg gag gca cag tgt                      1008
Ala Asp Leu Thr Gly Val Thr Val Gln Ser Pro Gly Glu Ala Gln Cys
                325                 330                 335 ctg ctg gga ccg gca gaa gct gaa ggg tct cag agg agg agg ctg ctg                      1056
Leu Leu Gly Pro Ala Glu Ala Glu Gly Ser Gln Arg Arg Arg Leu Leu
            340                 345                 350 gtt cca gca aat ggt gct gac ccc act gag act ctg atg ctg ttc ttt                      1104
Val Pro Ala Asn Gly Ala Asp Pro Thr Glu Thr Leu Met Leu Phe Phe
        355                 360                 365 gac aag ttt gca aac atc gtg ccc ttt gac tcc tgg gac cag ctc atg                      1152
Asp Lys Phe Ala Asn Ile Val Pro Phe Asp Ser Trp Asp Gln Leu Met
    370                 375                 380 agg cag ctg gac ctc acg aaa aat gag atc gat gtg gtc aga gct ggt                      1200
Arg Gln Leu Asp Leu Thr Lys Asn Glu Ile Asp Val Val Arg Ala Gly
385                 390                 395                 400 aca gca ggc cca ggg gat gcc ttg tat gca atg ctg atg aaa tgg gtc                      1248
Thr Ala Gly Pro Gly Asp Ala Leu Tyr Ala Met Leu Met Lys Trp Val
                405                 410                 415 aac aaa act gga cgg aac gcc tcg atc cac acc ctg ctg gat gcc ttg                      1296
Asn Lys Thr Gly Arg Asn Ala Ser Ile His Thr Leu Leu Asp Ala Leu
            420                 425                 430 gag agg atg gaa gag aga cat gca aaa gag aag att cag gac ctc ttg                      1344
Glu Arg Met Glu Glu Arg His Ala Lys Glu Lys Ile Gln Asp Leu Leu
        435                 440                 445 gtg gac tct gga aag ttc atc tac tta gaa gat ggc aca ggc tct gcc                      1392
Val Asp Ser Gly Lys Phe Ile Tyr Leu Glu Asp Gly Thr Gly Ser Ala
    450                 455                 460 gtg tcc ttg gag tga                                                                  1407
Val Ser Leu Glu *
465
```

```
<210> SEQ ID NO 4
<211> LENGTH: 84
<212> TYPE: DNA
<213> ORGANISM: Mus musculus

<400> SEQUENCE: 4
acagtctgta aggaaggaac ctggcaagac tcagaaaaca ggaaagaagt tgctggttcc      60
ggtaaacgga aacgactcag ctga                                            84

<210> SEQ ID NO 5
<211> LENGTH: 28
<212> TYPE: PRT
<213> ORGANISM: Mus musculus

<400> SEQUENCE: 5

Thr Val Cys Lys Glu Glu Pro Gly Lys Thr Gln Lys Thr Gly Lys Lys
 1               5                  10                  15

Leu Leu Val Pro Val Asn Gly Asn Asp Ser Ala Asp
            20                  25

<210> SEQ ID NO 6
<211> LENGTH: 27
<212> TYPE: PRT
<213> ORGANISM: Mus musculus

<400> SEQUENCE: 6

Thr Val Cys Lys Glu Gly Thr Trp Gln Asp Ser Glu Asn Arg Lys Glu
 1               5                  10                  15

Val Ala Gly Ser Gly Lys Arg Lys Arg Leu Ser
            20                  25
```